(12) United States Patent
Chu et al.

(10) Patent No.: US 11,185,255 B2
(45) Date of Patent: *Nov. 30, 2021

(54) SYSTEMS AND METHODS FOR MONITORING A PHYSIOLOGICAL PARAMETER OF PERSONS ENGAGED IN PHYSICAL ACTIVITY

(71) Applicant: Riddell, Inc., Des Plaines, IL (US)

(72) Inventors: Jeffrey J. Chu, Quechee, VT (US); Richard M. Greenwald, Norwich, VT (US); Jonathan G. Beckwith, Cornish, NH (US)

(73) Assignee: Riddell, Inc., Des Plaines, IL (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/167,056

(22) Filed: Oct. 22, 2018

(65) Prior Publication Data
US 2019/0090780 A1     Mar. 28, 2019

Related U.S. Application Data

(63) Continuation of application No. 13/603,319, filed on Sep. 4, 2012, now Pat. No. 10,105,076.
(Continued)

(51) Int. Cl.
*A61B 5/00*        (2006.01)
*A61B 5/103*      (2006.01)
(Continued)

(52) U.S. Cl.
CPC .............. *A61B 5/103* (2013.01); *A42B 3/046* (2013.01); *A61B 5/1114* (2013.01);
(Continued)

(58) Field of Classification Search
CPC ..... A61B 5/103; A61B 5/1114; A61B 5/4064; A61B 5/6803; A61B 5/746;
(Continued)

(56) References Cited

U.S. PATENT DOCUMENTS 3,646,606 A    2/1972   Buxton
3,845,389 A    10/1974   Phillips
(Continued)

FOREIGN PATENT DOCUMENTS

DE       19707495     8/1998
EP        0315498      5/1989
(Continued)

OTHER PUBLICATIONS

Greenwald, Richard M., Head Impact Severity Measures for Evaluating Mild Traumatic Brain Injury Risk Exposure, Apr. 2008, Neurosurgery, 62(4), pp. 789-798.
(Continued)

*Primary Examiner* — May A Abouelela
(74) *Attorney, Agent, or Firm* — Barnes & Thornburg LLP

(57) ABSTRACT

The present disclosure provides system and method for monitoring of at least one physiological parameter of a person engaged in a physical activity, for example, an impact received by a player engaged in a contact sport such as football. The system includes a monitoring unit that actively monitors the physiological parameter of the person, wherein the monitoring unit generates an alert event when the monitored physiological parameter exceeds a threshold of the parameter. The monitoring unit determines whether the parameter exceeds an over-exposure threshold, wherein said threshold is based upon both a single incidence or cumulative incidences.

32 Claims, 14 Drawing Sheets

Related U.S. Application Data

(60) Provisional application No. 61/533,038, filed on Sep. 9, 2011, provisional application No. 61/530,282, filed on Sep. 1, 2011.

(51) Int. Cl.
  *A42B 3/04* (2006.01)
  *A61B 5/11* (2006.01)
  *G16Z 99/00* (2019.01)
  *A61B 5/01* (2006.01)

(52) U.S. Cl.
  CPC .......... *A61B 5/4064* (2013.01); *A61B 5/6803* (2013.01); *G16Z 99/00* (2019.02); *A61B 5/01* (2013.01); *A61B 5/746* (2013.01); *A61B 5/7435* (2013.01); *A61B 2503/10* (2013.01); *A61B 2562/0219* (2013.01); *A61B 2562/0247* (2013.01); *A61B 2562/046* (2013.01)

(58) Field of Classification Search
  CPC .......... A61B 2562/046; A61B 2503/10; A61B 5/7435; A61B 5/01; A61B 2562/0219; A61B 2562/0247; A42B 3/046; G16Z 99/00; G06F 19/00
  USPC .......................... 600/300, 587, 595; 128/903
  See application file for complete search history.

(56) References Cited

U.S. PATENT DOCUMENTS

| | | | |
|---|---|---|---|
| 3,902,478 A | 9/1975 | Konopasek | |
| 3,972,038 A | 7/1976 | Fletcher | |
| 3,972,320 A | 8/1976 | Kalman | |
| 4,196,429 A | 4/1980 | Davis | |
| 4,250,894 A | 2/1981 | Frei | |
| 4,440,160 A | 4/1984 | Fischell | |
| 4,468,656 A | 8/1984 | Clifford | |
| 4,502,035 A | 2/1985 | Obenauf | |
| 4,590,801 A | 5/1986 | Merhav | |
| 4,608,998 A | 9/1986 | Murdock | |
| 4,665,748 A | 5/1987 | Peters | |
| 4,691,556 A | 9/1987 | Mellander | |
| 4,761,005 A | 8/1988 | French | |
| 4,763,275 A * | 8/1988 | Carlin | A42B 3/046 273/148 R |
| 4,763,284 A | 8/1988 | Carlin | |
| 4,873,867 A | 10/1989 | McPherson | |
| 4,883,271 A | 11/1989 | French | |
| 4,982,452 A | 1/1991 | Chaise | |
| 4,996,877 A | 3/1991 | Stewart | |
| 5,158,089 A * | 10/1992 | Swezey | A61B 5/1071 340/573.7 |
| 5,203,034 A | 4/1993 | Foehl | |
| 5,221,088 A | 6/1993 | McTeigue | |
| 5,287,562 A | 2/1994 | Rush | |
| 5,327,588 A | 7/1994 | Garneau | |
| 5,331,969 A | 7/1994 | Silberstein | |
| 5,348,008 A | 9/1994 | Bornn | |
| 5,372,365 A * | 12/1994 | McTeigue | A63B 24/0003 434/252 |
| 5,383,363 A | 1/1995 | Kulmaczewski | |
| 5,408,879 A | 4/1995 | Vreeburg | |
| 5,425,378 A * | 6/1995 | Swezey | A61B 5/1071 600/587 |
| 5,473,527 A | 12/1995 | Gold | |
| 5,487,305 A | 1/1996 | Ristic | |
| 5,524,894 A * | 6/1996 | Shannon | A63B 69/3608 33/366.15 |
| 5,539,935 A | 7/1996 | Rush, III | |
| 5,546,609 A | 8/1996 | Rush, III | |
| 5,596,491 A | 1/1997 | Gold | |
| 5,615,132 A * | 3/1997 | Horton | G06F 3/011 340/988 |
| 5,621,922 A | 4/1997 | Rush, III | |
| 5,645,077 A * | 7/1997 | Foxlin | A61B 5/1114 600/587 |
| 5,697,099 A | 12/1997 | Siska, Jr. | |
| 5,704,707 A | 1/1998 | Gebelein | |
| 5,723,786 A | 3/1998 | Klapman | |
| 5,745,028 A | 4/1998 | Hock | |
| 5,745,029 A | 4/1998 | Garcia | |
| 5,819,206 A | 10/1998 | Horton | |
| 5,856,811 A | 1/1999 | Shih | |
| 5,896,590 A | 4/1999 | Fleisch | |
| 5,916,181 A | 6/1999 | Socci | |
| 5,978,972 A | 11/1999 | Stewart | |
| 6,002,994 A | 12/1999 | Lane | |
| 6,009,563 A | 1/2000 | Swanson | |
| 6,032,530 A | 3/2000 | Hock | |
| 6,056,674 A | 5/2000 | Cook | |
| 6,057,758 A | 5/2000 | Dempsey | |
| 6,090,044 A | 7/2000 | Bishop | |
| 6,186,145 B1 | 2/2001 | Brown | |
| 6,198,394 B1 | 3/2001 | Jacobsen | |
| 6,204,813 B1 | 3/2001 | Wadell | |
| 6,259,944 B1 | 7/2001 | Margulis | |
| 6,298,483 B1 | 10/2001 | Schiebl | |
| 6,301,718 B1 | 10/2001 | Rigal | |
| 6,302,844 B1 | 10/2001 | Walker | |
| 6,331,168 B1 | 12/2001 | Socci | |
| 6,361,507 B1 | 3/2002 | Foxlin | |
| 6,366,871 B1 | 4/2002 | Geva | |
| 6,375,612 B1 | 4/2002 | Guichon | |
| 6,397,151 B1 | 5/2002 | Yamagishi | |
| 6,406,168 B1 | 6/2002 | Whiting | |
| 6,441,747 B1 | 8/2002 | Khair | |
| 6,484,133 B1 | 11/2002 | Vogt | |
| 6,530,884 B2 * | 3/2003 | Balkin | A61B 5/4806 600/300 |
| 6,539,336 B1 | 3/2003 | Vock | |
| 6,567,116 B1 | 5/2003 | Aman | |
| 6,588,022 B1 | 7/2003 | Anders | |
| 6,611,782 B1 | 8/2003 | Wooster | |
| 6,611,789 B1 | 8/2003 | Darley | |
| 6,647,787 B2 | 11/2003 | Fore | |
| 6,730,047 B2 | 5/2004 | Socci | |
| 6,735,551 B2 | 5/2004 | Voegeli | |
| 6,748,250 B1 | 6/2004 | Berman | |
| 6,798,392 B2 | 9/2004 | Hartwell | |
| 6,826,509 B2 | 11/2004 | Crisco, III | |
| 6,925,851 B2 | 8/2005 | Reinbold | |
| 6,964,638 B2 | 11/2005 | Theodoracopulos | |
| 7,054,784 B2 | 5/2006 | Flentov | |
| 7,087,015 B1 | 8/2006 | Comrie | |
| 7,092,846 B2 | 8/2006 | Vock | |
| 7,162,392 B2 | 1/2007 | Vock | |
| 7,386,401 B2 | 6/2008 | Vock | |
| 7,478,108 B2 | 1/2009 | Townsend | |
| 7,526,389 B2 | 4/2009 | Greenwald | |
| 7,548,168 B2 | 6/2009 | Ishikawa | |
| 7,693,668 B2 | 4/2010 | Vock | |
| 7,886,168 B2 * | 2/2011 | Lertora | G01P 1/127 713/320 |
| 8,280,681 B2 | 10/2012 | Vock | |
| 8,382,685 B2 | 2/2013 | Vaccari | |
| 8,468,613 B2 | 6/2013 | Harty | |
| 8,690,655 B2 | 4/2014 | Meyer | |
| 8,786,415 B2 | 7/2014 | Cavallaro | |
| 8,797,165 B2 | 8/2014 | Greenwald | |
| 8,860,570 B2 | 10/2014 | Thomas | |
| 9,141,759 B2 | 9/2015 | Burich | |
| 9,554,607 B2 | 1/2017 | Mack | |
| 9,566,471 B2 | 2/2017 | Deangelis | |
| 9,900,669 B2 | 2/2018 | Touma | |
| 10,071,282 B2 | 9/2018 | Deangelis | |
| 10,071,301 B2 | 9/2018 | Vock | |
| 10,182,135 B2 | 1/2019 | Black | |
| 10,292,650 B2 | 5/2019 | Greenwald | |
| 2002/0011250 A1 | 1/2002 | Stewart | |
| 2002/0024450 A1 | 2/2002 | Townsend | |
| 2002/0049507 A1 | 4/2002 | Hameen-Anttila | |
| 2002/0060633 A1 | 5/2002 | Crisco | |

(56) References Cited

U.S. PATENT DOCUMENTS

| | | |
|---|---|---|
| 2002/0087054 A1 | 7/2002 | Lin |
| 2002/0116147 A1 | 8/2002 | Vock |
| 2002/0183657 A1 | 12/2002 | Socci |
| 2003/0014210 A1 | 1/2003 | Vock |
| 2003/0071766 A1 | 4/2003 | Hartwell |
| 2003/0151554 A1 | 8/2003 | McCarthy |
| 2003/0163287 A1 | 8/2003 | Vock |
| 2003/0217582 A1 | 11/2003 | Reinbold |
| 2004/0008106 A1 | 1/2004 | Konczal |
| 2004/0225236 A1 | 11/2004 | Wheeler |
| 2004/0240198 A1 | 12/2004 | Laar |
| 2005/0177929 A1 | 8/2005 | Greenwald |
| 2006/0038694 A1 | 2/2006 | Naunheim |
| 2006/0074338 A1 | 4/2006 | Greenwald |
| 2007/0061106 A1* | 3/2007 | Vock ............... G01C 9/00 702/182 |
| 2010/0076321 A1 | 3/2010 | Zhang |
| 2010/0076692 A1 | 3/2010 | Vock |
| 2011/0125065 A1* | 5/2011 | Voronin ........... A61D 17/002 600/595 |
| 2011/0215931 A1 | 9/2011 | Callsen |
| 2011/0219852 A1* | 9/2011 | Kasten ............. G01L 5/0052 73/12.04 |
| 2012/0083714 A1* | 4/2012 | Yuen ............... A61B 5/4812 600/587 |
| 2012/0210498 A1 | 8/2012 | Mack |
| 2012/0220893 A1 | 8/2012 | Benzel |
| 2013/0060168 A1 | 3/2013 | Chu |
| 2013/0074248 A1 | 3/2013 | Evans |
| 2013/0110415 A1 | 5/2013 | Davis |
| 2013/0150684 A1* | 6/2013 | Cooner ............ A61B 5/0261 600/301 |
| 2013/0303946 A1* | 11/2013 | Gettens ............. A61B 5/11 600/587 |
| 2014/0288432 A1 | 9/2014 | Hennig |
| 2014/0364772 A1 | 12/2014 | Howard |
| 2015/0250250 A1 | 9/2015 | Ellis |
| 2017/0300755 A1 | 10/2017 | Bose |

FOREIGN PATENT DOCUMENTS

| | | |
|---|---|---|
| WO | 9836213 | 8/1998 |
| WO | 9904685 | 2/1999 |
| WO | 02053024 | 7/2002 |
| WO | 2006036567 | 4/2006 |

OTHER PUBLICATIONS

Duma, Stefan M., Analysis of Real-time Head Accelerations in Collegiate Football Players, Jan. 2005, Clin J Sport Med, vol. 15, No. 1, pp. 3-8.
Declaration from Nelson Kraemer regarding the discovery of the Radio Telemetry Project materials, Dec. 5, 2017 (2 pages).
Report No. 1062—Radio Telemetry Project, Progress Report No. 1, Jun. 9, 1964 (253 pages).
Report No. 1062—Radio Telemetry Project, Appendix A-C, Apr. 1963 (115 pages).
Report No. 1062—Radio Telemetry Project, Appendix D, Book 1, 1964 (108 pages).
Report No. 1062—Radio Telemetry Project, Appendix D, 1963 (159 pages).
Radio Telemetry Project Test Data, Aug. 25, 1964 (24 pages).
Radio Station License for Radio Telemetry Project, Jul. 7, 1965 (2 pages).
Operating Instructions for Radio Telemetry System, Apr. 1967 (10 pages).
Various Photographs related to Radio Telemetry Project, Oct. 1966 (84 pages).
Reid et al., Head Protection in Football, Sports Medicine, Mar./Apr. 1974, pp. 86-92.
Padgaonkar, A.J. et al., "Measurement of Angular Acceleration of a Rigid Body Using Linear Accelerometers," Journal of Applied Mechanics, Sep. 1975, pp. 552-556.
Moon, Donald W., et al., "Peak Head Acceleration of Athletes During Competition-Football," Medicine and Science in Sports, Spring 1971, vol. 3, No. 1, pp. 44-50.
Medendorp et al., Off-centric Rotation Axes in Natural Head Movements: Implications for Vestibular Reafference and Kinematic Redundancy, The American Physiological Society, 1998, pp. 2025-2039.
Foxlin et al., Miniature 6-DOF Inertial System for tracking HMDs, Apr. 13-14, 1998, SPIE, Helmet and Head-Mounted Displays III, AeroSense 98, vol. 3362.
Schatz, P., et al., "Computer-Based Assessment of Sports-Related Concussion", Applied Neuropsychology, 2003, vol. 10, No. 1, pp. 42-47.
King, A. I. et al., "Mechanics of the Head/Neck." The Biomedical Engineering Handbook: Second Edition. Dec. 28, 1999. CRC Press LLC. pp. 23-1:23-12.
Naunheim, Rosanne S., et al. "Comparison of impact data in hockey, football, and soccer." Journal of Trauma and Acute Care Surgery 48.5 (2000): 938-941.
Gibilisco, "Encode." The Illustrated Dictionary of Electronics. McGraw-Hill. 2001. Eighth edition. p. 257.
International Search Report for PCT/US2005/032903 dated Mar. 10, 2006.
International Search Report for PCT/US2006/000536 dated Oct. 2, 2006.
Murray, C., Smart Helmets Monitor Football Injuries, Dec. 18, 2003, Embedded.com.
Merono et al., Movement Evaluator System Via R.F. Transmission, 1995 IEEE, pp. 94-97.
Coleman et al., Ambient Head Temperature and Football Helmet Design, Mar. 1972, Medicine, Science, Exercise and Sports Journal, 19 pages.
Bai et al., A Portable ECG and Blood Pressure Telemonitoring System, Jul./Aug. 1999, IEEE Engineering in Medicine and Biology, pp. 63-70.
Puers et al., A Telemetry System for the Detection of Hip Prosthesis Loosening by Vibration Analysis, Aug. 25, 2000, Sensors and Actuators, vol. 85, pp. 42-47.
Written Opinion for PCT/US2006/000536 dated Jul. 10, 2007.
International Search Report and Written Opinion issued in PCT/US2019/066084 dated Mar. 9, 2020 (13 pages).

* cited by examiner

1400

LOWER SKILL LEVEL ALERT THRESHOLDS:

|  | DB | DL | LB |
|---|---|---|---|
| PLAYERS | 30 | 40 | 30 |
| IMPACTS | 14,000 | 28,000 | 24,000 |
| HITsp | T1 | T2 | T3 |

1410 — PLAYERS
1412 — IMPACTS
1416 — HITsp

UPPER SKILL LEVEL ALERT THRESHOLDS:

|  | DB | DL | LB |
|---|---|---|---|
| PLAYERS | 160 | 170 | 130 |
| IMPACTS | 127,300 | 324,000 | 150,000 |
| HITsp | T4 | T5 | T6 |

1510 — PLAYERS
1512 — IMPACTS
1516 — HITsp

FIG. 5

SYSTEMS AND METHODS FOR MONITORING A PHYSIOLOGICAL PARAMETER OF PERSONS ENGAGED IN PHYSICAL ACTIVITY

CLAIM OF PRIORITY UNDER 35 U.S.C. § 119

The present Application for Patent claims priority to Utility application Ser. No. 13/603,319, entitled "SYSTEMS AND METHODS FOR MONITORING A PHYSIOLOGICAL PARAMETER OF PERSONS ENGAGED IN PHYSICAL ACTIVITY," filed Sep. 4, 2012, Provisional Application No. 61/530,282, entitled "SYSTEMS & METHOD FOR MONITORING A PHYSIOLOGICAL PARAMETER OF PERSONS ENGAGED IN PHYSICAL ACTIVITY," filed Sep. 1, 2011, and Provisional Application No. 61/533,038, entitled "SYSTEMS & METHOD FOR MONITORING A PHYSIOLOGICAL PARAMETER OF PERSONS ENGAGED IN PHYSICAL ACTIVITY," filed Sep. 9, 2011, both of which are assigned to the assignee hereof and are hereby expressly incorporated by reference herein.

TECHNICAL FIELD

This disclosure relates to a system and method for monitoring of at least one physiological parameter of a person engaged in a physical activity, for example, an impact received by a player engaged in a contact sport such as football.

BACKGROUND

There is a concern in various contact sports, such as football, lacrosse and hockey, of brain injury due to impact to the head. During such physical activity, the head of the individual is often subjected to direct contact which results in impact to the skull and brain of the individual, as well as movement of the head or body part itself.

Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality. Almost all of what is known is derived from animal studies, studies of cadavers under specific directional and predictable forces (i.e. a head-on collision test), from crash a dummies, from human volunteers in well-defined but limited impact exposures or from other simplistic mechanical models. The conventional application of known forces and/or measurement of forces applied to animals, cadavers, crash dummies, and human volunteers limit our knowledge of a relationship between forces applied to a living human head and any resultant severe brain injury. These prior studies also have limited value as they typically relate to research in the automobile safety area.

The concern for sports-related injuries, particularly to the head, is higher than ever. The Center for Disease Control and Prevention estimates that the incidence of sports-related mild traumatic brain injury (MTBI) approaches 300,000 annually in the United States. Approximately one-third of these injuries occur in football, with MTBI being a major source of lost player time. Head injuries accounted for 13.3% of all football injuries to boys and 4.4% of all soccer injuries to both boys and girls in a large study of high school sports injuries. Approximately 62,800 MTBI cases occur annually among high school varsity athletes, with football accounting for about 63% of cases. It has been reported that concussions in hockey affect 10% of the athletes and make up 12%-14% of all injuries.

For example, a typical range of 4-6 concussions per year in a football team of 90 players (7%), and 6 per year from a hockey team with 28 players (21%) is not uncommon. In rugby, concussion can affect as many as 40% of players on a team each year. Concussions, particularly when repeated multiple times, significantly threaten the long-term health of the athlete. The health care costs associated with MTBI in sports are estimated to be in the hundreds of millions of dollars annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Athletes who suffer head impacts during a practice or game situation often find it difficult to assess the severity of the blow. Physicians, trainers, and coaches utilize standard neurological examinations and cognitive questioning to determine the relative severity of the impact and its effect on the athlete. Return to play decisions can be strongly influenced by parents and coaches who want a talented player back on the field. Subsequent impacts following an initial concussion (MTBI) may be 4-6 times more likely to result in a second, often more severe, brain injury. Significant advances in the diagnosis, categorization, and post-injury management of concussions have led to the development of the Standardized Assessment of Concussion (SAC), which includes guidelines for on-field assessment and return to play criteria. Yet there are no objective biomechanical measures directly related to the impact used for diagnostic purposes. Critical clinical decisions are often made on the field immediately following the impact event, including whether an athlete can continue playing. Data from the actual event would provide additional objective information to augment psychometric measures currently used by the on-site medical practitioner.

Brain injury following impact occurs at the tissue and cellular level, and is both complex and not fully understood. Increased brain tissue strain, pressure waves, and pressure gradients within the skull have been linked with specific brain injury mechanisms. Linear and rotational head accelerations are input conditions during an impact. Both direct and inertial (i.e. whiplash) loading of the head result in linear and rotational head acceleration. Head acceleration induces strain patterns in brain tissue, which may cause injury. There is significant controversy regarding what biomechanical information is required to predict the likelihood and severity of MTBI. Direct measurement of brain dynamics during impact is extremely difficult in humans.

Head acceleration, on the other hand, can be more readily measured; its relationship to severe brain injury has been postulated and tested for more than 50 years. Both linear and rotational acceleration of the head play an important role in producing diffuse injuries to the brain. The relative contributions of these accelerations to specific injury mechanisms have not been conclusively established. The numerous mechanisms theorized to result in brain injury have been evaluated in cadaveric and animal models, surrogate models, and computer models. Prospective clinical studies combining head impact biomechanics and clinical outcomes have been strongly urged. Validation of the various hypotheses and models linking tissue and cellular level parameters with MTBI in sports requires field data that directly correlates specific kinematic inputs with post-impact trauma in humans.

In the prior art, conventional devices have employed testing approaches which do not relate to devices which can be worn by living human beings, such as the use of dummies. When studying impact with dummies, they are typically secured to sleds with a known acceleration and impact velocity. The dummy head then impacts with a target, and the accelerations experienced by the head are recorded. Impact studies using cadavers are performed for determining the impact forces and pressures which cause skull fractures and catastrophic brain injury.

There is a critical lack of information about what motions and impact forces lead to MTBI in sports.

Most prior art attempts relate to testing in a lab environment. However, the playing field is a more appropriate testing environment for accumulating data regarding impact to the head. Previous research on football helmet impacts in actual game situations yielded helmet impact magnitudes as high as 530 g's for a duration of 60 msec and greater than 1000 g's for unknown durations, both with no known MTBI. Accelerometers were held firmly to the head via the suspension mechanism in the helmet and with Velcro straps. A recent study found maximum helmet accelerations of 120 g's and 150 g's in a football player and hockey player, respectively. The disparity in maximum values among these limited data sets demonstrates the need for additional large-scale data collection. A limitation of the prior art involves practical application and widespread use of measurement technologies that are size and cost effective for individuals and teams. Therefore, there would be significant advantage to outfitting an entire playing team with a recording system to monitoring impact activities. This would assist in accumulating data of all impacts to the head, independent of severity level, to study the overall profile of head impacts for a given sport. Also, full-time head acceleration monitoring would also be of great assistance in understanding a particular impact or sequence of impacts to a player's head over time that may have caused an injury and to better treat that injury medically.

To address this need, there have been many attempts in the prior art to provide a system for recording the acceleration and/or impact of an individual's body part, such as their head. For example, prior art systems have employed tri-axial accelerometers which are affixed as a module to the back of a football helmet. Such tri-axial accelerometers provide acceleration sensing in the X, Y and Z directions which are orthogonal to each other. Tri-axial accelerometer systems require that the accelerometers be orthogonal to each other. Also, such tri-axial accelerometer systems have been extremely expensive making it cost prohibitive for widespread commercial installation on an entire team. Prior art systems, have also attempted to precisely locate the various combinations of linear and rotational accelerometers, in specific orthogonal arrays, within a helmet to obtain complete three-dimensional head kinematics. Such arrays require that the accelerometers be positioned orthogonal to each other. It is impractical, from a size, cost and complexity standpoint, for commercial application of such arrays in helmet or head mounted systems.

Obviously, accelerometer arrays for measuring linear and rotational accelerations or pressure/force sensors for measuring pressure or force cannot be readily mounted inside the human head, as is done with instrumented test dummy heads. Other sensing technologies, such as gyroscopes, magneto hydrodynamic angular rate sensors and GPS sensors, do not currently fulfill the practical and technical specifications for a commercially available system. Also, the use of multi-axis accelerometer systems placed in a mouth guard are impractical for a number of reasons, including but not limited to positioning the mouth guard's battery in the user's mouth and the power required to transmit from inside the mouth exceeds FCC limits, any of which might present a hazard to the players and limited compliance among them.

In view of the foregoing, there is a demand for a physiological measuring system for players that can be manufactured and installed at very low cost to permit widespread utilization. There is a demand for a system that can be installed in the equipment of many individuals, such as an entire football team roster of over 60 players, to provide reliable monitoring and alerting of different types of impacts received by players during the course of play. Further, there is a demand for a system and method for measuring at least one physiological parameter of a player that is easy to install and comfortable for the individual to wear.

This disclosure solves the problems discussed above and other problems and provides advantages and aspects not provided by prior art of this type. A full discussion of the features and advantages of the present disclosure is deferred to the following detailed description, which proceeds with reference to the accompanying drawings.

SUMMARY

The present disclosure provides a system for monitoring of at least one physiological parameter of multiple players engaged in a contact sport. The system includes a plurality of monitoring units, each monitoring being associated with a specific player and having a sensor assembly that actively monitors at least one physiological parameter of the player while engaged in the contact sport to determine a physiological parameter value, wherein the monitoring unit selectively generates a first alert when the physiological parameter value exceeds a first predetermined threshold based upon a single incidence of the physiological parameter and a second alert when the physiological parameter value exceeds a second predetermined threshold based upon cumulative incidences of the physiological parameter. The system also includes a portable alert unit that receives the first alert and second alert transmitted from a particular monitoring unit and displays information relating to the particular alert to a user of the system.

An aspect of the disclosure provides wherein each monitoring unit is configured as an in-helmet unit positioned within in a protective helmet worn by a player engaged in the contact sport. Another aspect of the disclosure provides wherein the sensor assembly comprises a plurality of sensors formed from an electret film. Yet another aspect of the disclosure provides wherein the sensor assembly is positioned within an overliner that is wearable adjacent the player's head while the player is engaged in the contact sport. A further aspect of the disclosure provides a protective sports helmet worn by each player engaged in the contact sport, wherein the sports helmet includes an internal padding assembly and wherein the overliner is positioned between the player's head and the internal padding assembly when the sports helmet is worn by the player. Another aspect of the disclosure provides wherein the sensor assembly is operably connected to a control module, and the sensor assembly further comprises a front sensor positioned adjacent a front region of the sports helmet, a rear sensor positioned adjacent a rear region of the sports helmet, a left sensor positioned adjacent a left region of the sports helmet, a right sensor positioned adjacent a right region of the sports helmet and a top sensor positioned adjacent a top region of the sports helmet.

Still another aspect of the disclosure provides a protective sports helmet worn by each player engaged in the contact sport, wherein the physiological parameter actively monitored by the sensor assembly is the pressure resulting from an impact to the helmet worn by the player during play of the contact sport. Another aspect of the disclosure provides wherein the first predetermined threshold takes into account the player's skill level. A further aspect of the disclosure provides wherein the first predetermined threshold takes into account the player's position. Another aspect of the disclosure provides wherein the second predetermined threshold includes cumulative impact incidences occurring during a prior time interval. Still another aspect of the disclosure provides wherein an old impact incidence can be removed from a monitoring unit accumulator when they age beyond the prior time interval. Another aspect of the disclosure provides wherein a new impact incidence can be added to the monitoring unit accumulator and an old impact incidence is removed from the accumulator. A further aspect of the disclosure provides wherein the physiological parameter value is correlated to a multi-dimensional severity measure and then compared against the first predetermined threshold. Another aspect of the disclosure provides wherein the multi-dimensional severity measure includes inputs for linear acceleration and impact direction. Yet another aspect of the disclosure provides wherein the multi-dimensional severity measure includes inputs for the Head Injury Criterion and the Gadd Severity Index.

The disclosure also provides for using a weighted principal component score such as Head Impact Technology Severity Profile ($HIT_{SP}$) that takes into account linear acceleration, Head Injury Criterion (HIC), Gadd Severity Index (GSI), and impact direction.

Other features and advantages of the disclosure will be apparent from the following specification taken in conjunction with the following drawings. Implementations of the described techniques may include hardware, a method or process, or software for a mobile device on a computer-accessible medium.

The details of one or more implementations are set forth in the accompanying drawings and the description below. Other features will be apparent from the description and drawings, and from the claims.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 4 illustrates an exemplary table displaying HITsp exposure thresholds for a lower skill level of players.

FIG. 5 illustrates an exemplary table displaying HITsp exposure thresholds for a higher skill level players.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

It should be understood that the present disclosure relates generally to a system for actively monitoring at least one physiological parameter of players engaged in a sports activity, such as pressure or force on a body part (e.g., the head) and/or the acceleration of a body part (e.g., linear acceleration or rotational acceleration), both resulting from an impact or series of impacts to the player(s). The present disclosure, as will be discussed in detail below, is capable of monitoring any body part of an individual but has particular application in monitoring the human head. Therefore, any reference to a body part is understood to encompass the head and any reference to the head alone is intended to include applicability to any body part. For ease of discussion and illustration, discussion of the prior art and the present disclosure is directed to the head of human, by way of example and is not intended to limit the scope of discussion to the human head.

Figure 1A:
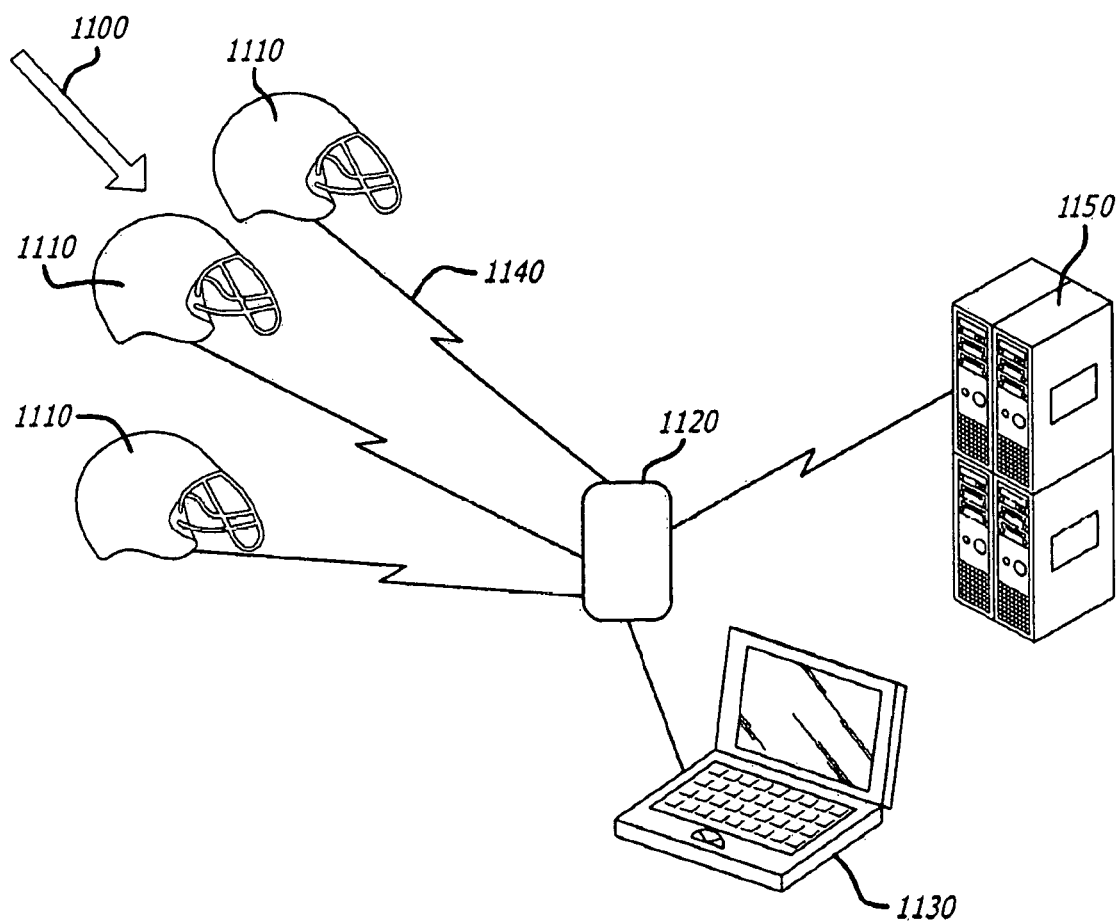
FIG. 1A illustrates an exemplary system in which a player helmet actively monitors physiological parameters of a player and generates alert events when the monitored physiological parameters exceed a threshold.

FIG. 1A illustrates an exemplary system 1100 in which a player helmet 1110 actively monitors at least one physiological parameter of a player and generates alert events when the monitored physiological parameter(s) exceed a threshold. Since most contact sports involve multi-player teams, the system 1100 simultaneously measures, records and transmits the data on the selected physiological parameter for all players on the team throughout the course of play, including a game or practice. System 1100 is especially well suited for helmeted team sports where players are susceptible to head impacts and injuries; for example, football, hockey, and lacrosse. The system 1100 could also be employed protective equipment other than helmets (e.g., shoulder pads or knee pads), or in sports where helmets are not traditionally worn; for example, rugby or soccer. The system 1100 could also be employed in military helmets, bike and motor sports, and winter sports (e.g. downhill skiing and ski jumping).

In one specific example, the system 1100 is configured to assess whether a particular impact or series of impacts received by a player exceeds two, weighted over-exposure thresholds based upon a single impact and/or cumulative impacts over a predefined amount of time (e.g., 7 days). These over-exposure thresholds are determined from the results of monitoring over 1,300 players using a system described in U.S. patent application Ser. Nos. 10/997,832; 11/225,880; and Ser. No. 11/328,445, wherein more than +1.4 million head impacts have been recorded to date and stored within a database. Using this database and proprietary algorithms, two types of over-exposure thresholds have been created—single event threshold and cumulative threshold.

When configured for helmeted team sports, such as football, the system 1100 includes at least player helmet 1110, an alert unit 1120, and a user terminal 1130 (see FIG. 1A). The player helmet 1110, includes an in-helmet unit (or monitoring unit) 1200 that is configured to monitor and analyze both single and cumulative impacts to the player wearing the player helmet 1110 (see FIG. 1B). The impact data may be correlated to a multi dimensional severity measure (e.g., weighted principal component score such as Head Impact Technology Severity Profile ($HIT_{SP}$) that takes into account linear acceleration, Head Injury Criterion (HIC), Gadd Severity Index (GSI), and impact direction. The impact severity may also be weighted by impact location.

In one embodiment, the in-helmet unit (or monitoring unit) 1200 measures a physiological parameter, such as pressure resulting from the helmet impact, and weighs this value by impact location to determine the severity level of the received impact and then compares it against the HITsp threshold programmed inside the in-helmet unit (or monitoring unit) 1200. In another embodiment, the in-helmet unit 1200 measures multiple physiological parameters, such as the impact pressure and acceleration (such as linear and/or rotational acceleration) resulting from the impact(s). The in-helmet unit 1200 may also measure different modalities, for example, both piezo and electret film within the in-helmet unit 1200 can measure changes in temperature and other mechanical stress due to sound and/or air pressure. This provides the ability to measure simultaneous effects using a single sensor, such as an impact to a player and the player's temperature, for example. Impact data is continually monitored for a value from any channel 1220*a-e* that exceeds a predetermined threshold programmed into the in-helmet unit 1200. Once triggered, a microcontroller wakes up and collects data from all channels 1220*a-e*. Impact data may be stored in an analog domain in the in-helmet unit 1200 using peak hold circuits, and peak hold values may be collected from each channel 1220*a-e*. If any channel data exceeds the predefined threshold, that data is processed further to determine a calculated value. If the calculated value exceeds the predefined single impact alert threshold, then the alert, namely the single impact alert, is sent. If the calculated value is not peak magnitude alertable (i.e., it is below the alert threshold), then the calculated value is evaluated to determine if it should be added to the cumulative calculation. If the calculated value is added to the cumulative calculation, the processed cumulative value is compared to the predetermined cumulative impact alert threshold. If the processed cumulative value exceeds that alert threshold, then a cumulative alert (or multiple impact alert) is sent to the remote alert unit 1120. The system 1100 may be configured such that only one cumulative alert for a particular player can be sent per day. The system 1100 may also be configured to include the player's medical history and/or injury history as part of the impact monitoring, threshold calculation and/or alert criteria. For example, if a specific player has a known medical condition, then the system 1100 may take that condition into account when performing the threshold calculation and/or sending an alert to the remote unit 1120. Also, the remote unit 1120 may be configured to also display that player's medical condition when displaying the single impact alert and/or the cumulative impact alert.

As an example regarding the single event, peak overexposure may be determined in which each individual peak channel recorded is scaled to a calibration value determined at the time of manufacturing. Subsequently, each individual channel is transformed into a HITsp value based on the individual channel location using a $3^{rd}$ order polynomial. Finally the HITsp values from the peak individual channel along with physically adjacent channels are summed together to provide a final Hasp severity measure. For example, if the peak channel (i.e. highest magnitude) is the left channel, adjacent values from the top, front, and back are included in the final HITsp severity measure. As an example regarding a cumulative event, cumulative exposure may be determined in which only data that are above a 95% threshold for an individual's playing position and skill level are included in the calculation of cumulative exposure. This threshold may be based on a proprietary database consisting of millions of impacts from thousands of players. With each impact that is added to a monitoring unit accumulator or database cumulative bucket, the monitoring unit accumulator or cumulative bucket magnitude decreases based on an exponential decay function. This final cumulative value is compared to an alerting threshold based on playing position and skill level.

Using these over-exposure thresholds, system 1100 can identify when a player has sustained a single impact or series of impacts that are atypical for their skill level and/or playing position. Thus, single impacts and/or multiple impacts can be weighted based upon the player's (wearer's) skill level, playing level or both. The skill level can be divided into lower levels and upper levels. The lower levels include, for example, youth and high school players. The upper levels include, for example, college and professional players. The playing positions can be defined by well-recognized positions, including offensive line, running backs, quarterback, wide receivers, defensive linemen, linebackers, defensive backs and special teams. The playing positions could also be defined by the player's attributes, including neck size, age, head size, weight, and body mass index. Over-exposure alerts give sideline staff members an indication that an abnormal physiological parameter result (e.g., head contact has occurred and the potential for injury may exist). When the system 1110 is configured to monitor head impacts, this allows team staff to identify players who are prone to atypical head contact and/or styles of play that lead to over-exposure. Essentially, system 1100 acts as an on-field set of eyes that can continually monitor players where the sideline personnel, including coaches and trainers can not.

The system 1100 is configured to monitor impacts, determine the severity level of a received single impact or cumulative impacts and then makes a comparison of that severity level against a threshold value of a comparative metric to provide a "single impact alert" and/or a "cumulative impact alert." The comparator employed by the system 1100 can be linear acceleration, a combination of linear acceleration and other measured values, or a combination of accelerations, values and constants. Preferably, the system 1100 utilizes "HITsp" as the comparator, wherein HITsp is a composite variable that combines measures of linear acceleration, rotational acceleration, and impact duration into a single metric that is then weighted by impact location. While not diagnostic of injury, HITsp has been shown to be more sensitive and specific to diagnosed concussion than any of the component measures alone. Specifically, HITsp has been shown to be 50% more sensitive to predict a subsequently diagnosed concussion than usage of any individual measure by itself (e.g., linear acceleration). The published paper, titled *HEAD IMPACT SEVERITY MEASURES FOR EVALUATING MILD TRAUMATIC BRIAN INJURY RISK EXPOSURE*, the entire content of which is incorporated herein by reference, describes this method in greater detail and is attached as Appendix A. In the following description, the system 1110 utilizes the HITsp as the comparator for threshold analysis. However, as noted above, other thresholds or combination of thresholds may be used. When a calculated parameter result approaches or exceeds a predetermined level or threshold determined by HITsp, the system 1100 notifies the qualified sideline personnel and utilize the method of the present disclosure to evaluate and treat the player(s) in question. At the proposed thresholds, HITsp is more sensitive to a diagnosed concussion than monitoring linear acceleration.

As discussed below, the in-helmet unit 1200 comprises a novel sensor assembly 1220 and control module 1230 (see FIGS. 1B, 1C and 2). The system 1100 can be configured for use with a protective shoulder pad assembly worn by a player engaged in the contact sport, wherein the monitoring unit 1200 is incorporated in the shoulder pad structure, including the protective arches that overlap the player's shoulder, chest and back regions. In a preferred embodiment, the rotational acceleration component of an impact is not measured by the sensor assembly 1220, however, the rotational acceleration component is included in the HITsp comparator. An alert event occurs if the in-helmet unit 1200 determines that the severity level of the received impact exceeds the HITsp threshold for a single impact and/or cumulative impacts. The in-helmet unit 1200 generates an alert and communicates the alert to the alert unit 1120 through the communication link 1140. An over exposure condition is defined as either sustaining a single impact severity in the predetermined threshold percentile (e.g., 99 percentile) for that skill level and player position, or exceeding cumulative impacts severity calculated over a predefined period of time (e.g., 7 days) for that player skill level and player position, as described in more detail below. Thus, the in-helmet unit 1200 provides an alert to the alert unit 1120 based upon an evaluation of single impact and cumulative impacts, weighted in light of the player's skill level and the player's position.

The alert unit 1120 receives the alert and displays it to the sideline personnel bearing the alert unit 1120. For each alert, the alert unit 1120 displays the affected player's identity, for example by name or jersey number, the measured parameter, and the time of the alert event. However, the player's identity can be protected by use of a unique player identifier, which may be encoded and/or encrypted. For example, encoding the signals or data with a unique identifier enables the system 1100, namely the alert unit 1120, to properly decode and/or multiplex information from the various in-helmet units 1200 simultaneously transmitting alerts and/or data. As another example, the parameter data may be encrypted to increase the security of the underlying data, such as by using a cipher for performing encryption and decryption, and a key to parameterize the cipher. The time stamp of the alert event allows sideline personnel and medical staff to correlate the calculated parameter to actual videotape of the sporting event that led to the alert event. Once an alert event has occurred, the in-helmet unit 1200 can send a signal to the alert unit 1120 that alerts the sideline personnel to employ a method for evaluating and treating the player in question, as explained below. The player in question is quickly identified by the in-helmet unit 1200 due to the unique identifier provided by the in-helmet unit 1200 and the subsequent recognition of the identifier and the multiplexing performed by the alert unit 1120. In this manner, the sideline personnel including those bearing the alert unit 1120 can efficiently evaluate the player in question from among the many players comprising the team. The alert unit 1120 can take the form of portable handsets, smart-phones or personal digital assistants, although they may be implemented in other form factors. Program applications, including an application for evaluating and treating players based upon the results of alerts communicated to the alert unit 1120 can be configured to execute on many different types of alert unit 1120.

The system 1100 also includes a user terminal 1130, such as a custom user device, a laptop, a tablet computer or a smartphone, for example. The user terminal 1130 may be programmed with Player Management Software (PMS) that allows various components of system 1100 to communicate and interact and that provides the coach all information necessary for operating system 1100. The user terminal 1130 may connect to the alert unit 1120 via a wired or a wireless connection. In one example, the alert unit 1120 connects to the user terminal 1130 via a USB connection. In interacting with the PMS, user informs the software that the users wishes to add a new player helmet 1110 to a list of player helmets 1110 monitored by the alert unit 1120. As a result, PMS launches a wizard that advises the user to place the in-helmet unit 1200 into a configuration state by holding down the button on the control module 1230 for prolonged period of time (e.g., 5 seconds). A fast flashing yellow LED on the control module 1230 confirms this state. The in-helmet unit 1200 remains in this state for 30 seconds. The user then clicks the "next" button in PMS that begins configuration setup on the in-helmet unit 1200 through the alert unit 1120 acting as a modem. Configuration setup may include obtaining the unique serial number of the in-helmet unit 1200 and storing it in a database for later association with a specific player. The configuration setup also may include assigning an appropriate RF parameter for enabling communication between the in-helmet unit 1200 and the alert unit 1120. The database may be located at the alert unit 1120 or may be located remote from the alert unit but accessible to the alert unit 1120 via wired or a wireless connection. For example, the database may correspond to the database 1150. The PMS confirms successful configuration.

In one example, the communication link 1140 is wireless utilizing RF communication protocol based on time division multiplexing approach. In approximately every 9.6 seconds, the alert unit 1120 broadcasts a ping 75 times every 30 ms. After each ping, the alert unit 1120 listens for an in-helmet unit 1200 that is scheduled to respond at a specific ping set and time slot. There are two time slots per ping where an in-helmet unit 1200 can respond. The ping plus time slot listen period is a "superframe." At setup, the PMS configures the in-helmet unit 1200 with the appropriate RF info (e.g. channel, PAN ID, etc) as well as a timeslot within a superframe. Since communications are happening asynchronously and the actual communication time is in a small window, the in-helmet unit 1200 wakes up periodically at some multiple of ping windows (the 75 superframes). If it hears a ping from it's alert monitor, the in-helmet unit 1200 calculates the time required to wakeup on the next ping cycle (9.6 sec+an offset it calculates to wakeup right before the appropriate superframe). After an in-helmet unit 1200 checks in with the alert unit 1120, the alert unit 1120 responds with an acknowledgment. Included in this acknowledgment is the player threshold information. The alert unit 1120 updates threshold information from the PMS when the user syncs. Upon the next communication with the in-helmet unit 1200, the alert unit 1120 communicates this information to the alert unit 1120. The in-helmet unit 1200 monitors the impacts to the player wearing the in-helmet unit 1200 and reports an alert to the alert unit 1120 if the impacts exceed the threshold of the comparator, on single impact basis or cumulative impact basis.

Figure 1B:
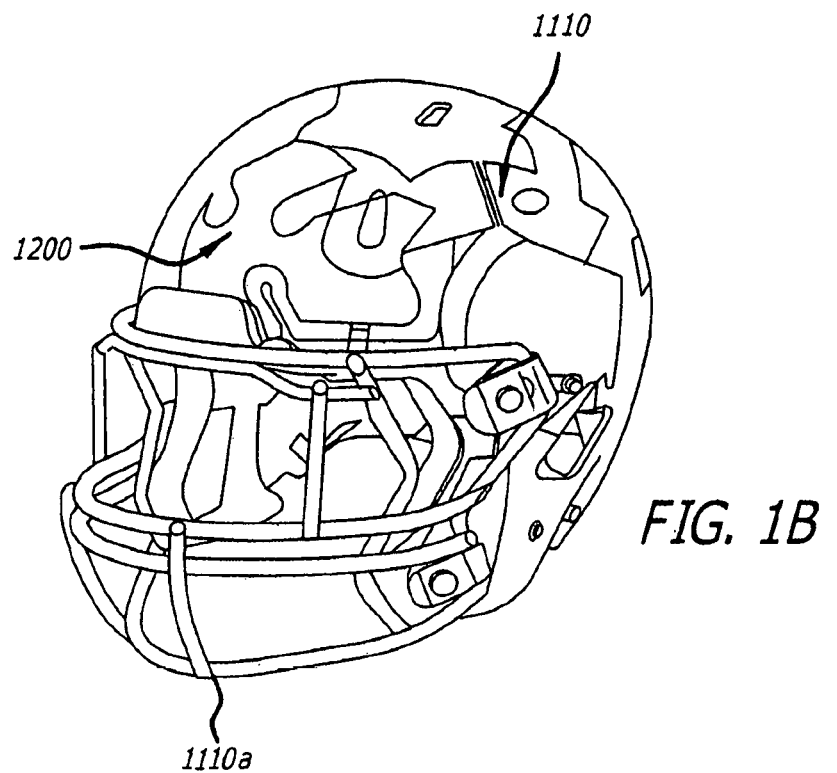
FIGS. 1B-1C illustrate different views of player helmet shown in FIG. 1A.
Figure 1C:
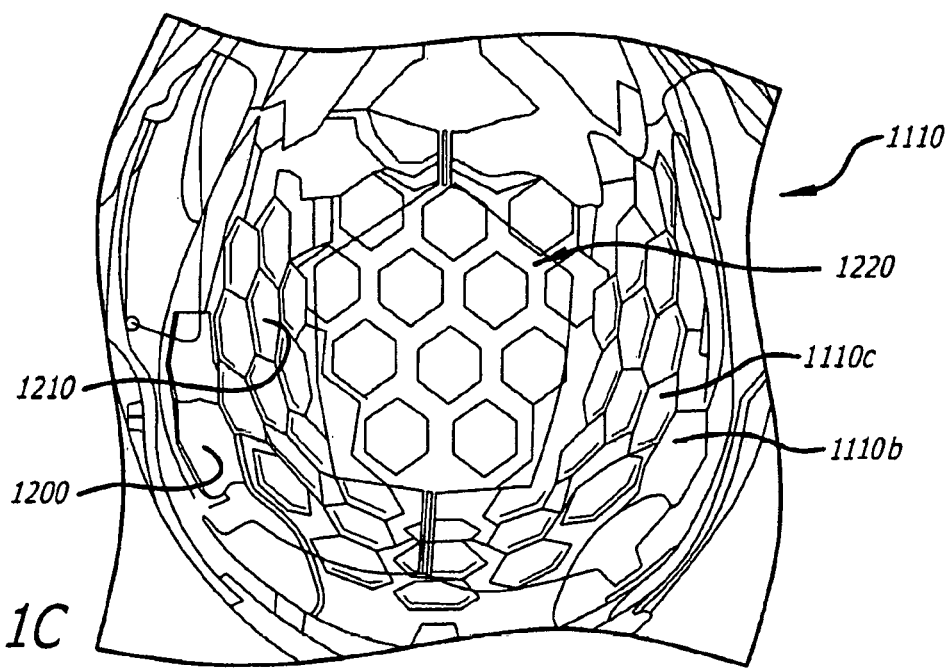
Figure 2:
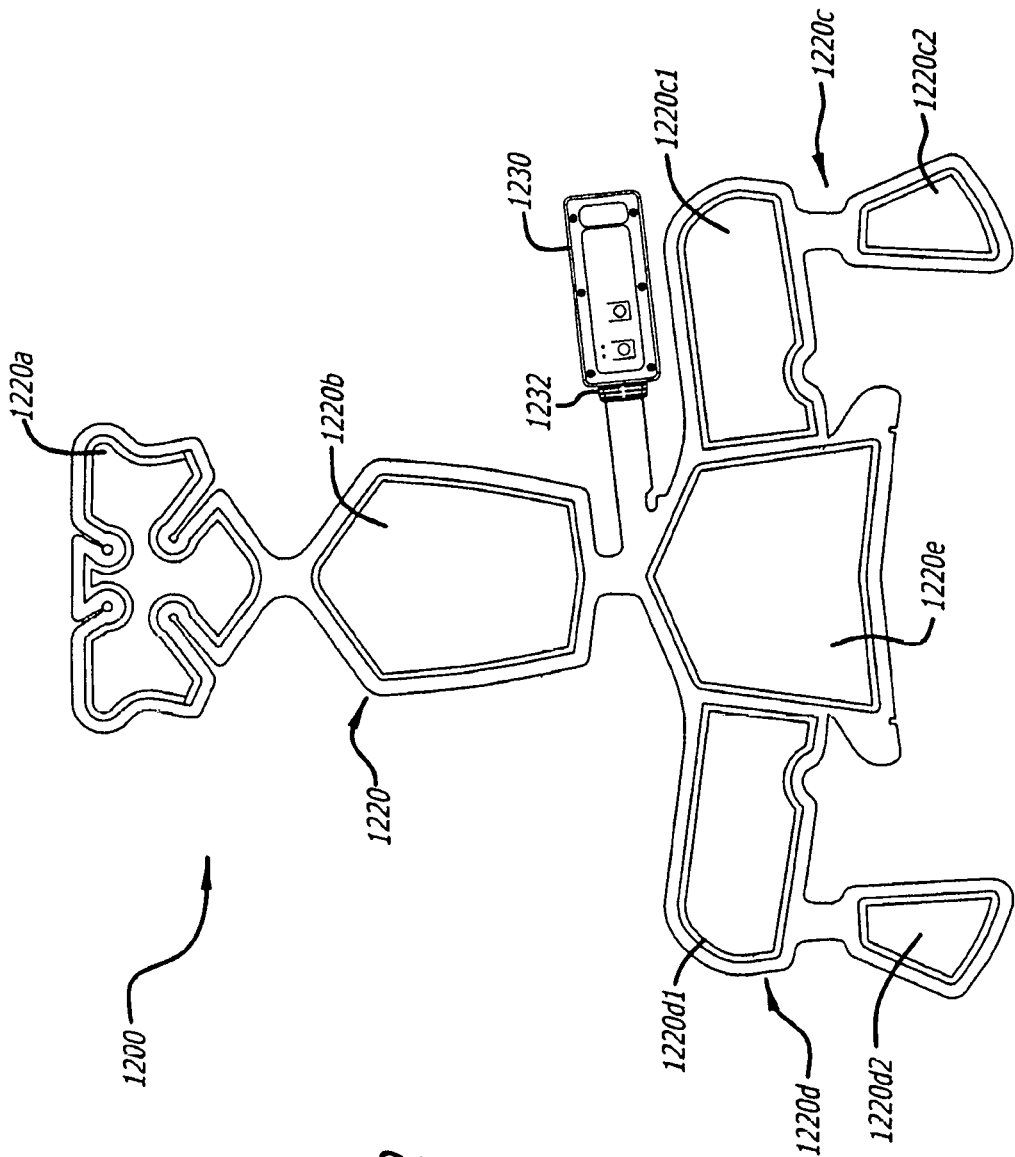
FIG. 2 illustrates an exemplary IHU that fits within the player helmet shown in FIG. 1A.

FIG. 1B illustrates an enlarged view of the player helmet 1110. FIG. 1C illustrates an interior of the player helmet 1110. As shown, player helmet 1110 includes the face guard 1110a, primary internal padding assembly 1110b, and an overliner 1110c. The overliner 1110c is configured to include the in-helmet unit (IHU) 1200, a secondary padding assembly 1210 (which preferably has a thinner configuration than the primary internal pad assembly 1110b). Alternatively, the secondary padding assembly 1210 is omitted from the overliner 1110c. In FIG. 2, the in-helmet unit 1200 includes a sensor assembly 1220 and a control module 1230 connected to the sensor assembly 1220 via a connector 1232. The sensor assembly 1220 includes five sensors 1220a, 1220b, 1220c, 1220d, and 1220e that each provide distinct electrical channels. As shown, sensors 1220c and 1220d each have a horizontal component 1220c1, 1220d1, and a vertical component 1220c2, 1220d2. The in-helmet unit 1200 is fitted within the overliner 1110c and when the overliner 1110c is positioned within the player helmet 1110, the overliner 1110c rests on the players head. Accordingly, the sensor assembly 1220 is between the secondary pad assembly 1210 and the primary internal pad assembly 1110b. To this end, the sensor assembly 1220 does not directly touch the player's head. In a slightly different implementation, the sensor assembly 1220 is fitted on the front side (or interior portion) of the overliner 1110c such that when the overliner 1110c is positioned within the player helmet 1100, the sensor assembly 1220 is adjacent to the player's head. In yet another implementation, the overliner 1110c is omitted and the sensor assembly 1220 is integrated with the primary internal pad assembly 1110b, wherein the sensor assembly 1220 is positioned within the housing members that form the internal pad assembly 1110b. Alternatively, the sensor assembly 1220 is integrally formed as part of the housing that comprises the internal pad assembly 1110b.

In one implementation, the sensors 1220a-1220e of the sensor assembly 1220 are formed from an electret film, which has a unique, strong electromechanical response to an impact(s) to the helmet 1110. The film is based on a polyolefin material manufactured in a continuous biaxial orientation process that stretches the film in two perpendicular directions (machine direction and the transverse direction). Further the film is expanded in thickness at high-pressure gas-diffusion-expansion (GDE) process. The structure of electret film consists of flat voids separated by thin polyolefin layers. Typically the electret film is 70-80 μm thick. The voids are made by compounding small particles, which function as rupture nuclei and form closed lens like cavities to the film during the biaxial orientation. The voids are enlarged at with the GDE process, which more than doubles the thickness and elasticity of the film by increasing the size of air-voids inside it. Electromechanical response with GDE processed film is over 10-fold compared to non-swelled film. A permanent electric charge is injected into the material by corona charging it in high electric field. This causes electric breakdowns occur inside the material, thus charging the void interfaces inside the film in order to form an electret material capable of interacting with its environment. Thin metal electrodes are, for example, arranged by screen-printing them first to 75-100 μm polyester film and laminating together with electret film. Vacuum evaporation to both surfaces of the film is also possible for actuator purposes. Other typical ways to arrange electrodes is using aluminum-polyester laminate and etching the electrode pattern prior laminating with electret film. In another implementation, the sensors 1220a-1220e are made of piezoelectric material. Two very distinct forms of piezoelectric materials were evaluated and characterized during impact: Polyvinylidene Flouride (PVDF) and Lead Ziconate Titanate (PZT). PZTs are ceramic discs with a high piezoelectric constant, but are extremely fragile. In contrast, PVDF is a polmner that exhibits piezoelectric effects and can be silkscreened onto flexible substrates (e.g., Mylar®) in an ultrathin coating creating a flexible sensor and vastly improved durability.

Although the in-helmet unit 1200 is shown and described to include five sensors 1220a-e, one of ordinary skill in art recognizes that the in-helmet unit 1200 may have more or less sensors. The number of sensors may depend on the application and the information that is required to meet the needs of the application. For monitoring at least one physiological parameter of player engaged in a sports activity, for example a football player, the impact location as part of impact severity calculation is important. Therefore, the in-helmet unit 1200 includes five distinct sensors 1220a-e for five distinct regions (e.g., top, left, right, front, and back) of the helmet 1100, which also corresponds to the player's head regions. Each sensor 1220 provides an electrical channel for helmet impact data acquisition and processing. For off-center impacts (as opposed to on-center impacts), the system 1100 includes algorithms that can evaluate the ratio of impact energy recorded by adjacent channels to estimate to a higher resolution (approximately 10 degrees). When an impact to the helmet 1110 is detected by multiple sensors, only data from the closest sensor to the impact location and the sensors adjacent to the closest sensor is used in the weighting calculation. For example, when an off-center impact is received on the helmet 1100 and the back sensor 1220e and left sensor 1220c detected equal impact energy without significant energy from other sensors, then the impact location is determined by the system 1100 to be directly between the back sensor 1220e and left sensor 1220c. Also, if the impact location is on the left side of the helmet 1110, the system 1100 will combine usable data from the left 1220c, front 1220a, top 1220b, and rear 1220c sensors for the weighting calculation, but any data recorded by the right 1220d sensor will be ignored. Similarly, when an on-center impact is applied to the front of the helmet 1110, any data from the rear sensor 1220e is ignored. Accordingly, the system 1110 is configured to selectively utilize data from a limited number of the sensors 1220a-e while disregarding other, essentially irrelevant sensor data, based upon the location of the impact to the helmet 1110.

The system 1100 is also configured to monitor impacts and process data from players who experience multiple impacts on the same play. A person of skill in the art of designing sophisticated monitoring equipment for contact sports recognizes that many football players, including running backs, offensive lineman and defensive lineman, experience multiple impacts on a single play. For example, when a running back receives multiple impacts while carrying the football (e.g., a rushing play), every impact detected by the sensors 1220 is compared to the HITsp thresholds, as long as a specified time (e.g., 60 ms) has passed between impacts. In the context of the running back receiving two impacts, if both detected impacts exceed the single event impact threshold, each impact is treated as an independent peak overexposure alert and the alert unit 1120 provides the alert described above. For each alertable event, the alert unit 1120 provides the alert relevant information, including the type of alert, the time of alert (down to milliseconds), and the unique player identifier that sustained the impacts in question. It is contemplated that any other type of relative information may be included in the alert that is sent, such as impact or temperature date, for example.

In another application, where impact location is not necessary, a single sensor may be used. A single sensor in this context would still have sufficient material to mostly cover the surface of the head, but would electrically appear as one channel. The sensor assembly 1220 automatically and continuously measures and records the player's physiological parameters and transmits data regarding the parameter to the control module 1130. The control module 1230 is operably connected to each of sensors 1220a-1220e via a separate wire lead or channel.

Figure 3:
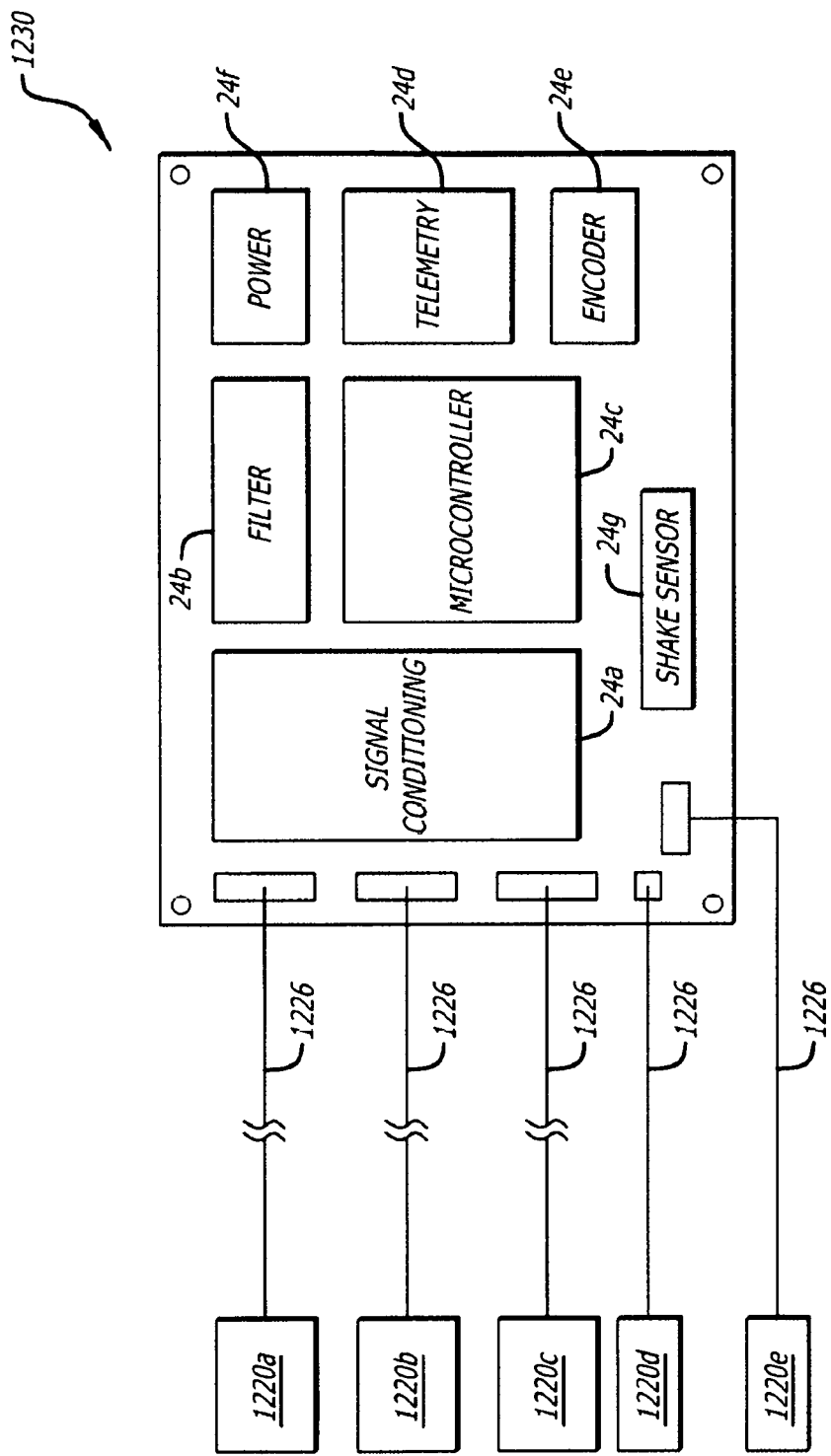
FIG. 3 illustrates a schematic of the IHU shown in FIG. 2.

FIG. 3 illustrates a schematic of the IHU 1200. As shown, the control module 1230 is connected via a separate wire lead 1226 to each of sensors 1220a-1220e. The control module 1230 includes a signal conditioner 24a, a filter 24b, a microcontroller 24c (or microprocessor), a telemetry element 24d, an encoder 24e, and a power source 24f. The control module 1230 includes a shake sensor 24g that may be used to turn the in-helmet unit 1200 ON or OFF based on a specific shake pattern of the player helmet 1110. For example, hitting and/or shaking the player helmet 1110 once may turn it ON; whereas, hitting and/or shaking the player helmet 1110 twice may turn it OFF or vice versa. Alternatively, the player helmet 1110 may have control buttons, such as a power button and a configuration button, for example. The in-helmet unit 1200 has low power requirements, providing for long battery life, thereby optimizing the continued use of the in-helmet unit 1200. For example, in normal operation (e.g., continuous monitoring for alertable impacts), the in-helmet unit 1200 may consume about 12-20 uA. In a deep sleep state (e.g., everything is off except time keeping), the in-helmet unit 1200 may consume about 8 uA. In an alert state (e.g., the in-helmet unit 1200 is trying to send an alert to the alert unit 1120) the in-helmet unit 1200 may consume about 1-5 mA.

As mentioned above, the control module 1230 is configured to perform various impact calculations and send an alert to an alert unit 1120 when a predetermined threshold is exceeded. The control module 1230 enables continued monitoring and analysis of head impacts on two basis: single impact and cumulative impacts. Both single impact analysis and cumulative impact analysis may take into account player's position (e.g., quarterback, linebacker, and running back in football, for example) and player's skill/playing level (e.g., elementary, high school, college or professional). The control module 1230 sends an alert to the alert unit 1120 for all impacts exceeding single impact over-exposure threshold. The single impact over-exposure threshold may be at the level that is inclusive of diagnosed concussion. Additionally, the single impact over-exposure threshold may be at the level that are typically experienced during play (e.g., warning that excessive exposure has occurred). To this end, the single impact over-exposure threshold may be set at the 99th percentile of impact exposure for two weighting factors: skill level (youth, high school, NCAA, Pro) and position (DB, DL, LB, OL, QB, RB, ST, WR). The 99th percentile of impact exposure may be obtained from teams associated with different skill level.

As another example, to measure the player's temperature, each in-helmet unit 1200 includes at least one temperature measuring sensor such as a thermistor, which comprises resistive circuit components having a high negative temperature coefficient of resistance so that the resistance decreases as the temperature increases. Alternatively, the temperature sensor is a thermal ribbon sensor or a band-gap type integrated circuit sensor. To measure both the acceleration and temperature of the player's body part, the sensors can be a combination of accelerometers and thermistors operably connected to the control module 1230. Where the system 1100 is configured for use with a football team to measure and monitor head acceleration and player body temperature, the sensors are accelerometers and thermistors that are arrayed in an in-helmet unit 1200 for each player. To measure other physiological parameters, such as the player's heart rate and blood pressure, the sensors are micro electromechanical system (MEMS) type sensors that use auscultatory (e.g., listening to the internal sounds made by the body) and/or oscillometric (e.g., oscillations of the arterial pulse) measurement techniques. In another embodiment, the sensors may include low acceleration (low G) accelerometers that are configured to measure small movements of the player's head consistent with balance problems. The system 1100 includes an algorithm that calculates and observes a player's balance between plays or during extended stoppages in play, such as when a penalty is being assessed or a timeout. In this manner, the player's physiological parameter can be measured on the field of play, instead of the sideline. When a player assumes the ready position prior to the commencement of the play, for example a three-point stance, the low G accelerometers and the algorithm would detect player movements indicative of balance problems and a concussion.

In an embodiment where the system 1100 monitors each player's body temperature, the alert unit 1120 receives data from the in-helmet units 1200 and then calculates each player's body surface temperature, the rate of temperature increase and/or decrease versus a selected time interval. In addition to the temperature sensor, the system 1100 can include an additional temperature and/or humidity sensor to measure ambient conditions and use the resulting data for correction purposes. When the system 1100 is configured for player body temperature monitoring in helmeted team sports, the in-helmet unit 1200 can be positioned within the helmet 1100 or within other protective equipment worn by each player, such as a shoulder pad assembly. The alert unit 1120 receives the temperature data from each in-helmet unit 1200 and then applies an algorithm to calculate the player's body surface temperature, the rate of temperature increase and/or decrease, and other temperature-based parameters that aid in the evaluation of player thermal management.

FIG. 4 provides a table 1400 displaying the HITsp exposure thresholds for a lower level skill level of players (e.g., high school players) for various player positions (e.g., defensive backs (DB), defensive line (DL) and linebacker (LB)). The number of lower level players for each of the three positions is provided, as well as the total number of impacts for each player position. Data from additional players in different positions (offensive line, quarterback, running back, wide receiver, and special teams) was obtained but is not included in FIG. 4. The data in table 1400 was collected from players among 12 teams using the systems and methods described in U.S. patent application Ser. Nos. 10/997,832; 11/225,880; and Ser. No. 11/328,445. The table 1400 includes players row 1410, impacts row 1412, and the HITsp exposure threshold row 1416 for specific player positions, wherein the threshold T1-T3 can be set by the system operator (e.g., the 99th percentile) and subsequently adjusted. Applicants have determined that the HITsp exposure threshold T1-T3 varies with player position, i.e., among defensive backs, defensive linemen and linebackers.

FIG. 5 provides a table 1500 displaying the HITsp exposure thresholds for a higher skill level of players (e.g., college and/or professional players) for defensive backs (DB), defensive line (DL) and linebacker (LB) player positions. The number of upper level players for each of the three positions is provided, as well as the total number of impacts for each player position. Data from additional players in different positions (offensive line, quarterback, running back, wide receiver, and special teams) was obtained but is not included in FIG. 5. The exemplary table 1500 was collected from the prior monitoring of numerous football teams. The table 1500 includes players row 1510, impacts row 1512, and the HITsp exposure threshold row 1516, wherein the threshold T4-T6 can be set by the system operator (e.g., the 99th percentile) and subsequently adjusted. Applicants have determined that the HITsp exposure threshold T4-T6 varies with player position, i.e., among defensive backs, defensive linemen and linebackers. Applicants have also determined that between the player positions, the HITsp exposure thresholds for the higher skill level players exceed the thresholds for the lower level skill players.

The control module 1230 sends an alert to the alert unit 1120 when a cumulative impact to the player over the defined period of time exceeds the multiple impact over-exposure threshold, even if none of the individual impact exceeds the single impact threshold. The cumulative impacts correspond to multiple impacts over a defined period of time. The defined period of time corresponds to seven days in one specific example. The accumulation process may assign a "weight" to older impacts. The accumulation process also allows for removal of older impacts that are beyond the time period to allow for newer impacts to be added. Applicants have determined that alerts based upon cumulative over-exposure increases sensitivity of the system 1100 to diagnosed concussion by a considerable amount.

Figure 6:
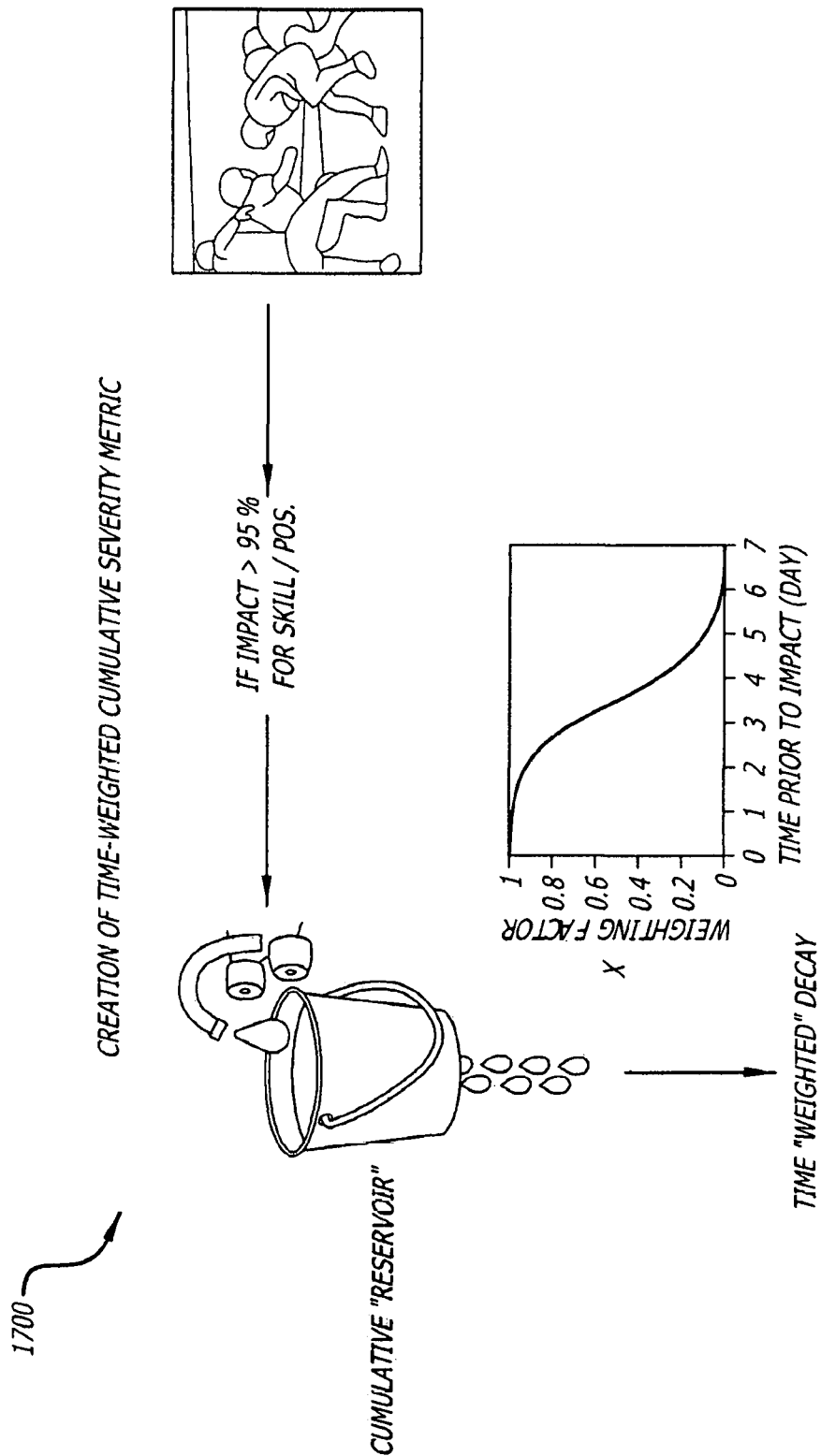
FIG. 6 illustrates an exemplary flow for creation of time-weighted cumulative severity metric.

FIG. 6 illustrates an exemplary flow 1700 for creation of time-weighted cumulative severity metric. As shown, if the impact is greater than 95 percentile for the given skill level and position, the impact is recorded in a database (e.g., shown as a bucket for illustrative purposes). Overtime, the impact is subjected to time "weighted" decay to reduce the level of impact. For example, the impact that recorded 4 days ago may be multiplied by 0.4 weighting factor, thereby reducing the level of impact. Once the cumulative impact recorded in the database exceeds the multiple impact over-exposure threshold, the alert is generated and sent to the alert unit 1120. The cumulative impact increases sensitivity for "delayed diagnosis" concussion, which are typically associated with lower peak severity. In one example, "delayed diagnosis" concussions means concussions that were not directly diagnosed following an observed impact and instead were diagnosed later in the day or the next day. Impact associated with the "delayed diagnosis" is the maximum severity impact of the day. One skilled in the art recognizes that weighting variables (e.g., time window, decay function, input threshold) are adjustable. The control module 1230 may be housed inside translucent housing.

Figure 7A:
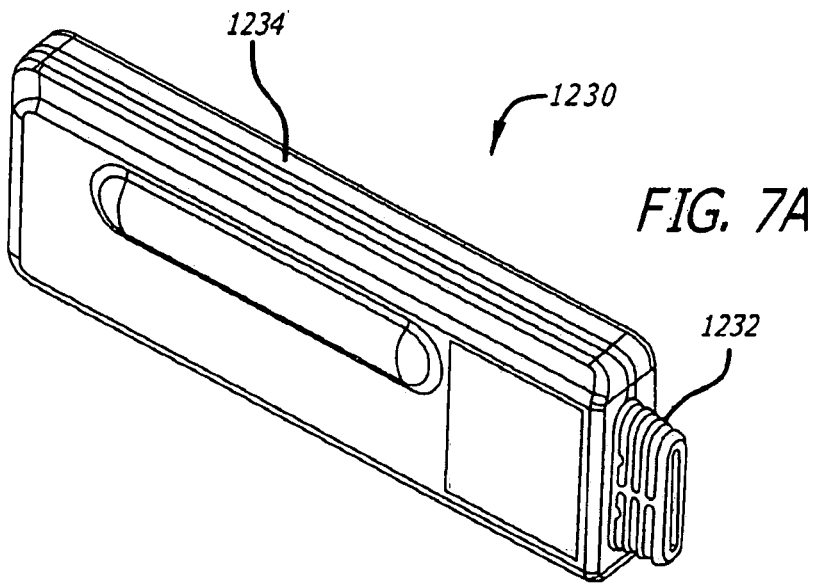
FIGS. 7A-7C illustrate an exemplary control module shown in FIG. 2.
Figure 7B:
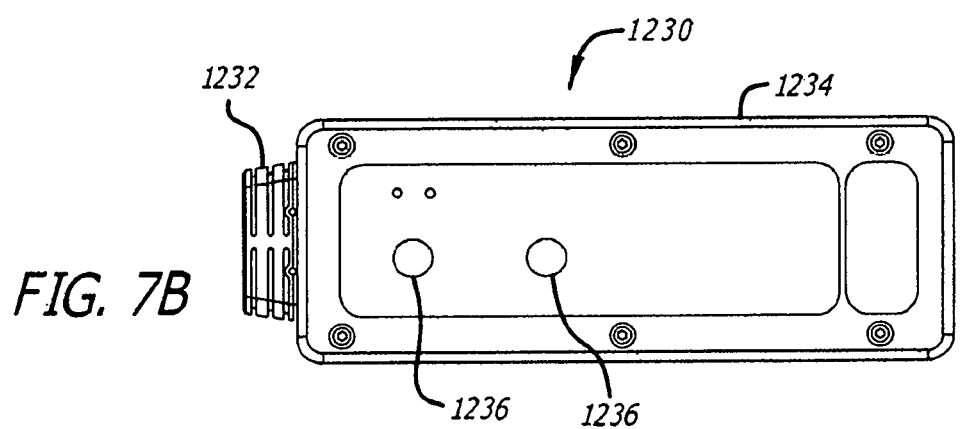
Figure 7C:
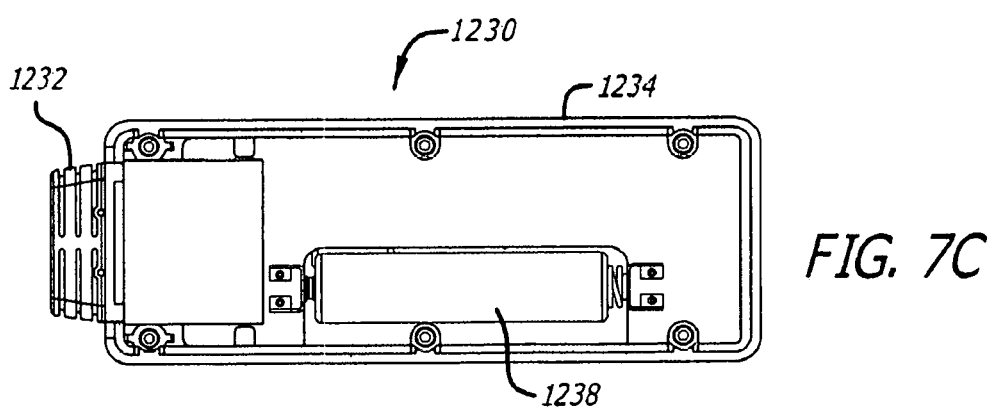

FIGS. 7A-7C illustrate an exemplary control module 1230. FIG. 7A illustrates a perspective view of the control module 1230 having a housing 1234 and a connector 1232. FIG. 7B illustrates a front view of the control module 1230 with LED indicators 1236 to show operational or connectivity status, such as successful pairing of the control module 1230 with its corresponding alert unit 1120. FIG. 7C is a rear view of the control module 1230 with the rear portion of the housing 1234 removed. A battery 1238 provides power to the control module 1230 and may be a standard sized battery, thereby allowing for cost effective and simple replacement.

The control module 1230 may send an alert to the alert unit 1120 for all impacts exceeding single impact over-exposure threshold. Similarly, the control module 130 may send an alert to the alert unit 1120 when a cumulative impacts to the player over the defined period of time exceed the multiple impact over-exposure threshold even if none of the individual impact exceeds the single impact threshold.

To support simultaneous transmissions from multiple control modules 1230, the signals sent from each control module 1230 can be divided with any suitable division process, such as time division multiple access (TDMA), code division multiple access (CDMA), or frequency division multiple access (FDMA) technology, for example. As a TDMA example, up to four teams may be assigned to any one computer at an institution. Each team may communicate with up to 150 players simultaneously. A team may have up to two alert monitors per team or eight alert monitors in total assigned to the computer. A team may be defined as freshman, junior varsity (JV), varsity or varsity offense, varsity defense, for example. Users may define whatever construct they want. Players assigned to teams are not heard or seen by alert monitors from a different team. Each team is assigned a different operating channel based on the 802.15.4 standard operating within the 2.4 Ghz band. Two alert monitors per team may co-exist and may simultaneously receive alerts from players. For example, it takes approximately 2.4 seconds for an alert monitor to scan for 150 player units. To accommodate simultaneous receipt of an alert, alert monitors initially wake up listening for other alert monitors in close vicinity. If the newly woken alert monitor hears another alert monitor in close vicinity, the newly woken alert monitor is able to determine the next available scan period. If an alert monitor scans every 9.6 seconds for about 2.4 seconds, this allows up to four alert monitors to co-exist in a TDMA scenario. For example, this leaves two alert monitors per team (e.g. visitor and home) to co-exist.

Figure 8A:
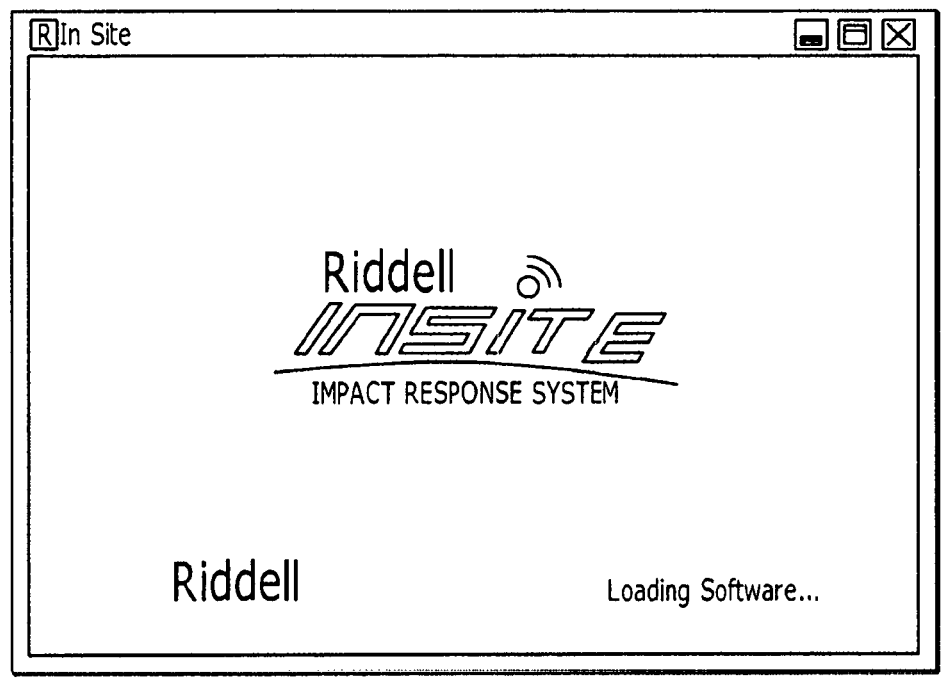
FIGS. 8A-8I illustrate an exemplary process for starting the PMS and assigning a player helmet to a specific alert unit shown in FIG. 1A.

FIGS. 8A-8I illustrate an exemplary process for starting the PMS and assigning a in-helmet unit 1200 to a specific alert unit 1120. FIG. 8A illustrates an exemplary User Interface (UI) 2000A that is demonstrated to the user upon activation of the PMS. The PMS may be activated by selection of its respective icon on the user terminal 1130.

Figure 8B:
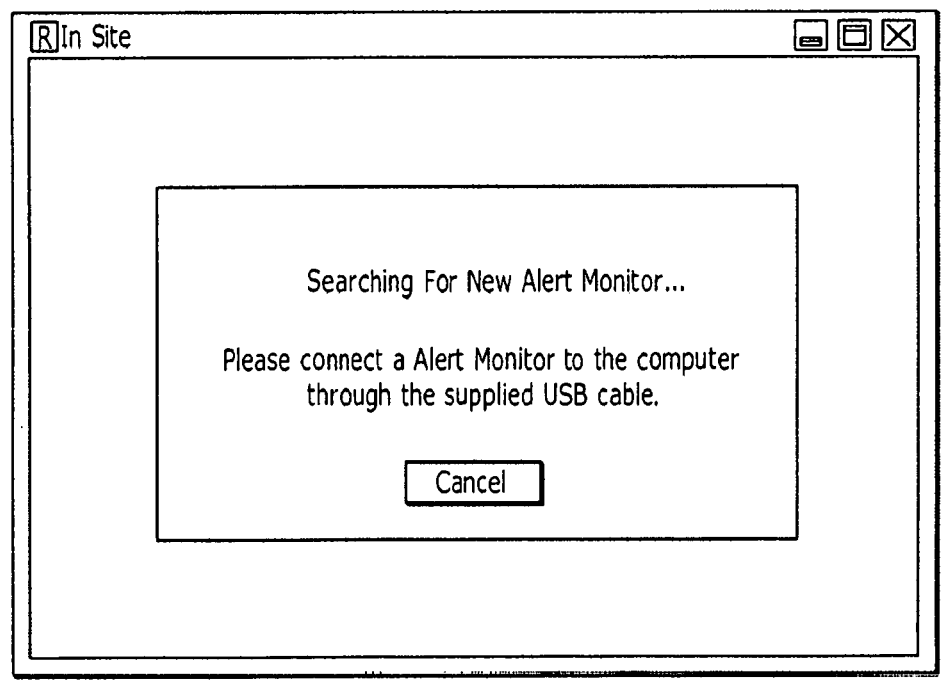

FIG. 8B illustrates an exemplary UI 2000B informing the user that PMS is searching for a new alert unit 1120. The UI 2000B requests the user to connect an alert unit 1120 to the user terminal 1130. The alert unit 1120 may be connected to the user terminal 1130 via a USB connection. When the user connects the alert unit 1120 to the user terminal 1130, PMS automatically brings up the "Adding a New Alert Unit" Wizard.

Figure 8C:
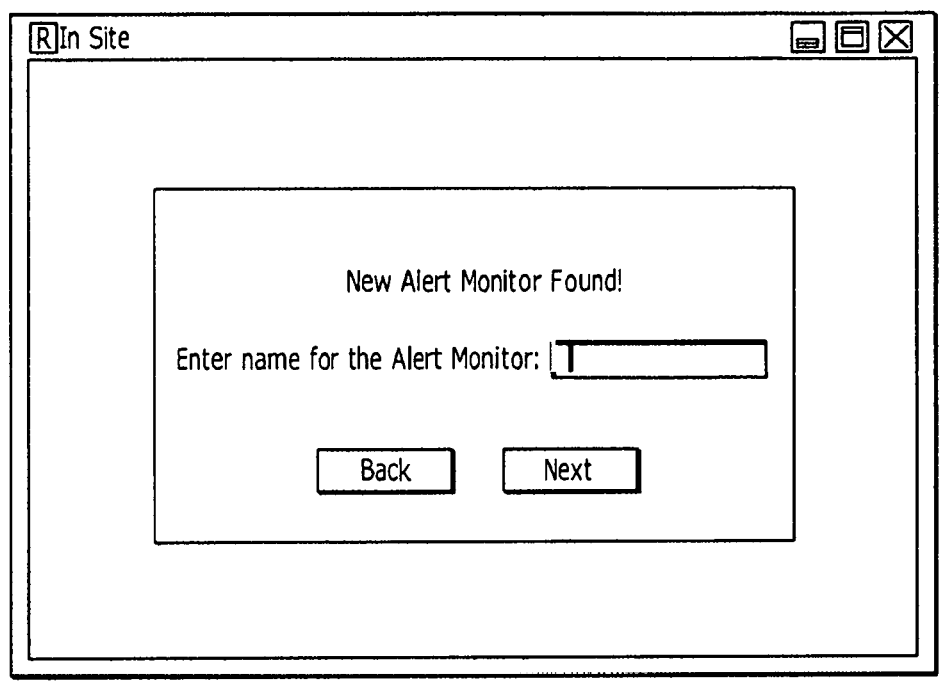

FIG. 8C illustrates an exemplary UI 2000C informing the user that the alert unit 1120 has been detected. The UI 2000C also requests that the user name the alert unit 1120 for easy alert monitoring management and clicks next. To this end, if the user has more than one alert unit 1120, the user may disconnect the alert unit 1120 and connect the second alert unit 1120 and repeater this process until the user has added all new alert units 1120 and named them. Then, the user can move on to configuring the player helmets 1110.

Once the user completed the alert unit 1120 wizard, the user can configure the in-helmet unit 1200 using the player helmet wizard. First, the user has to make sure that the control module 1230 is connected to the sensor assembly 1220 of the IHU 1200 inside the helmet overliner (overliner can be in or outside of the helmet). Upon connecting the control module 1230 with the sensor assembly 1220, the user should see a red light blink 3 times to indicate the power is connected. Then, the user should ensure that the user terminal 1130 is connected to one of the alert units 1120 and alert unit wizard is completed. Once the alert unit wizard is completed, the player helmet wizard appears on the user's PC display. The player helmet wizard may also appear when the user configures new in-helmet unit 1200 while working with the PMS.

Figure 8D:
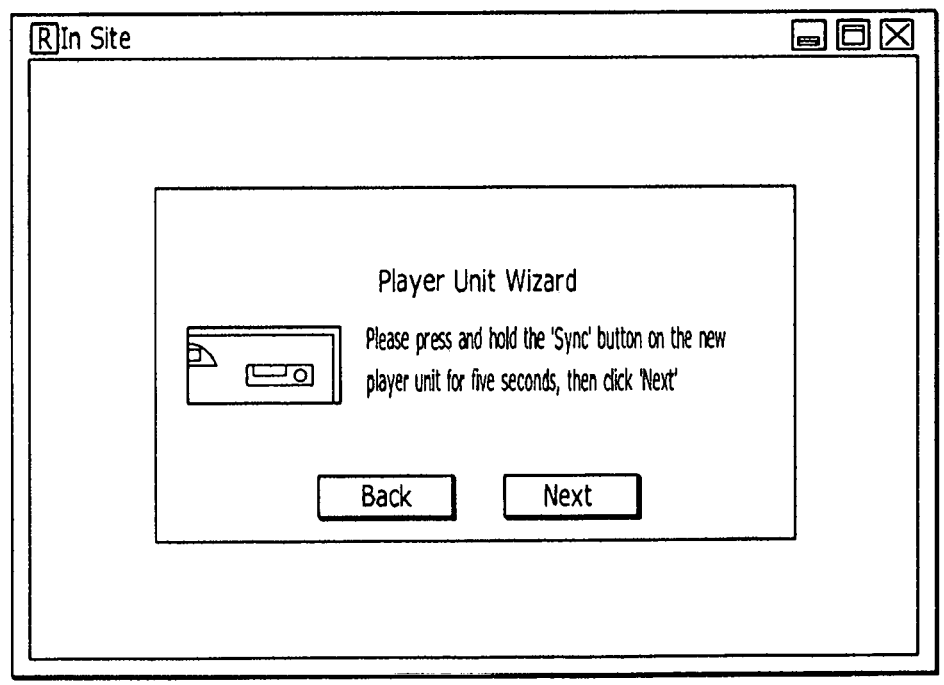

The player helmet wizard displays "equipment assignments" tab selection of which allows the user to add a player helmet. If the user wishes to add more player helmets the user may select a "+" button within the "equipment assignments" window. To synchronize the player helmet that have been assigned to a specific alert unit 1120, the player helmet wizard instructs the user to press the round "Sync" button on the in-helmet unit 1200 until the orange light starts blinking quickly. FIG. 8D illustrates an exemplary UI 2000D instructing the user to hold the "Sync" button on the in-helmet unit 1200 for five seconds to enable the in-helmet unit 1200 to be associated with the alert unit 1120 connected to the user terminal 1130.

Figure 8E:
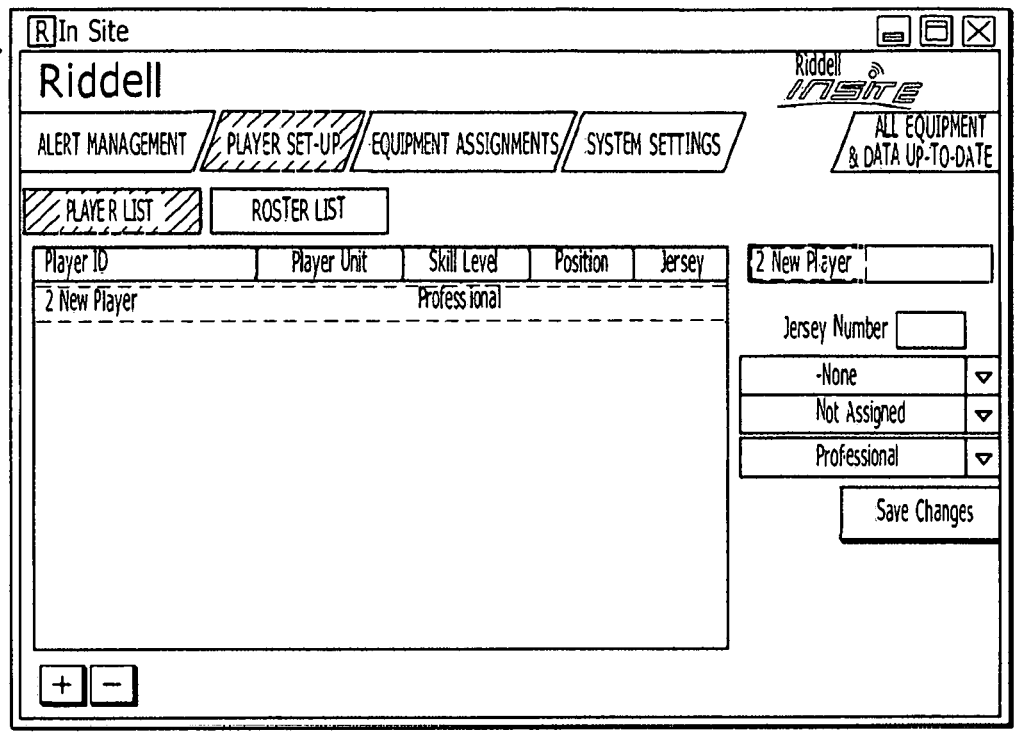

FIG. 8E illustrates an exemplary UI 2000E allowing the user to assign a new player to the added in-helmet unit 1200. To add a new player, the UI 2000E instructs the user to "Player Set-up" tab and select "Player List" tab within a window generated as a result of selection of "Player Set-up" tab. The user may select the "+" button at the bottom of the window to insert a player into the list of players. From there, the user can name the player's jersey number, which may be used for alert identification. Additionally, the user may select the drop down box in this window to select the player's position, assign a in-helmet unit 1200 to the player from among the various in-helmet units 1200 that have been added to PMS. To this end, in-helmet units 1200 that have been added to the system will automatically appear on the drop down list. Additionally, the user may select the drop down box to identify the player's playing level. After identification of these criteria for the player, the user can save the changes and can click "+" button add more players to the system.

Figure 8F:
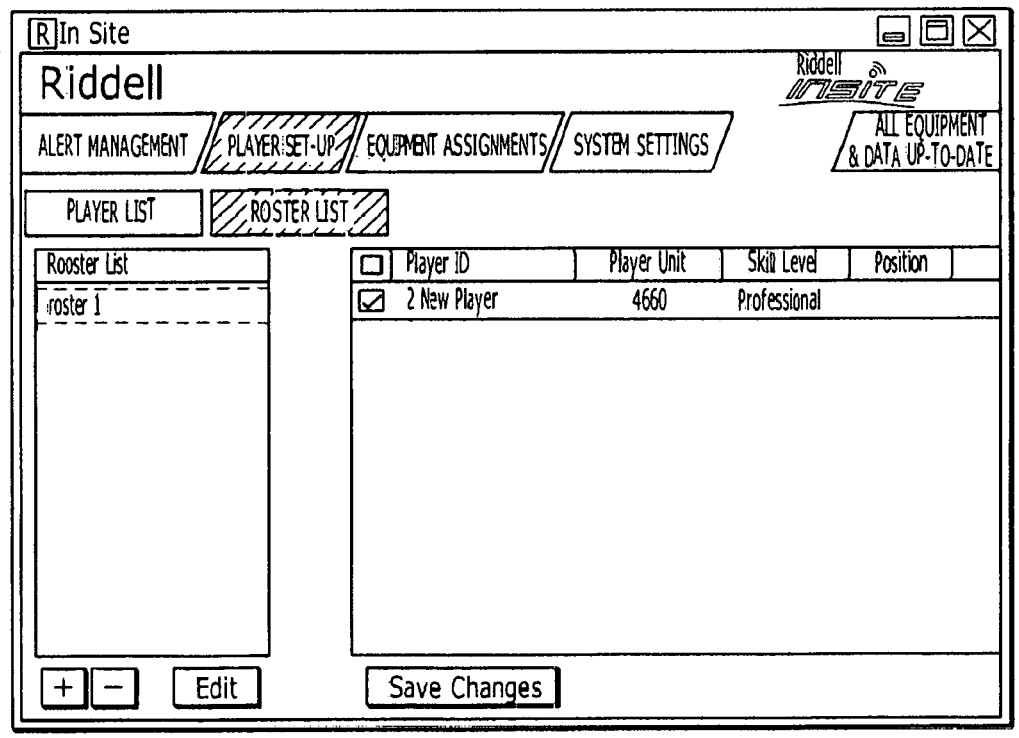

FIG. 8F illustrates an exemplary UI 2000F allowing the user to create a roster. Rosters can include the whole team or subsets of teams (e.g., offense, defense, JV, freshman, etc.). To create a roster, the user will select the "Roster List" tab. In keeping with the previous example, the user selects "+" button appearing on the window generated as a result of the selection of the "Roster List" tab to create a new roster. Then, as shown in UI 2000F, using the check box to the left of the player ID, the user selects the player the user wishes to have in the roster and save the changes. In one implementation, only the players with an assigned player helmet and position will be listed among the list of drop down menu.

Figure 8G:
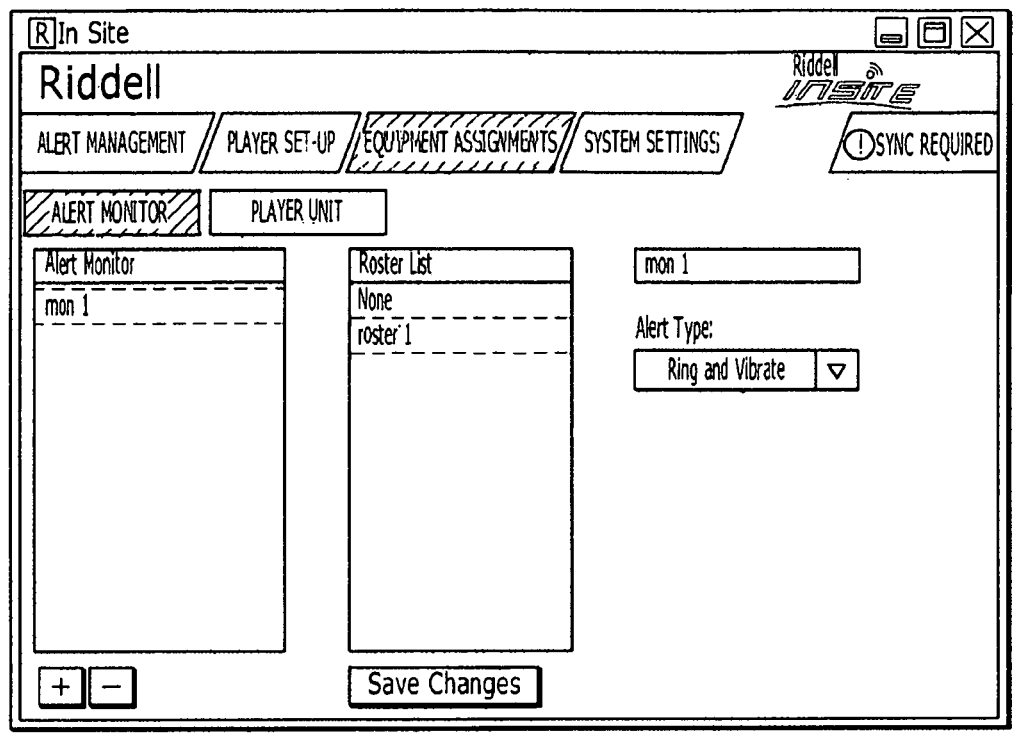

FIG. 8G illustrates an exemplary UI 2000G allowing the user to assign the roster to an alert unit 1120. After creating the roster, the user should assign it to the alert unit. To do so, the user may go to "Equipment Assignments" tab and select "Alert Monitor" tab within the window generated by selection of "Equipment Assignments" tab. Then, the user may click on the alert monitor option and the roster list that it be paired to. As shown, in UI 2000G, alert unit "mon1" is paired with "roster 1." The user may then click "Save Changes" button. Additionally, the user can change the alert type for this alert unit using the drop down box on the right of UI 2000G. Next, to communication this information to the player helmet, the user should synchronize. The "SYNC REQUIRED" tab in the top right will change color to indicate that a sync is required.

Figure 8H:
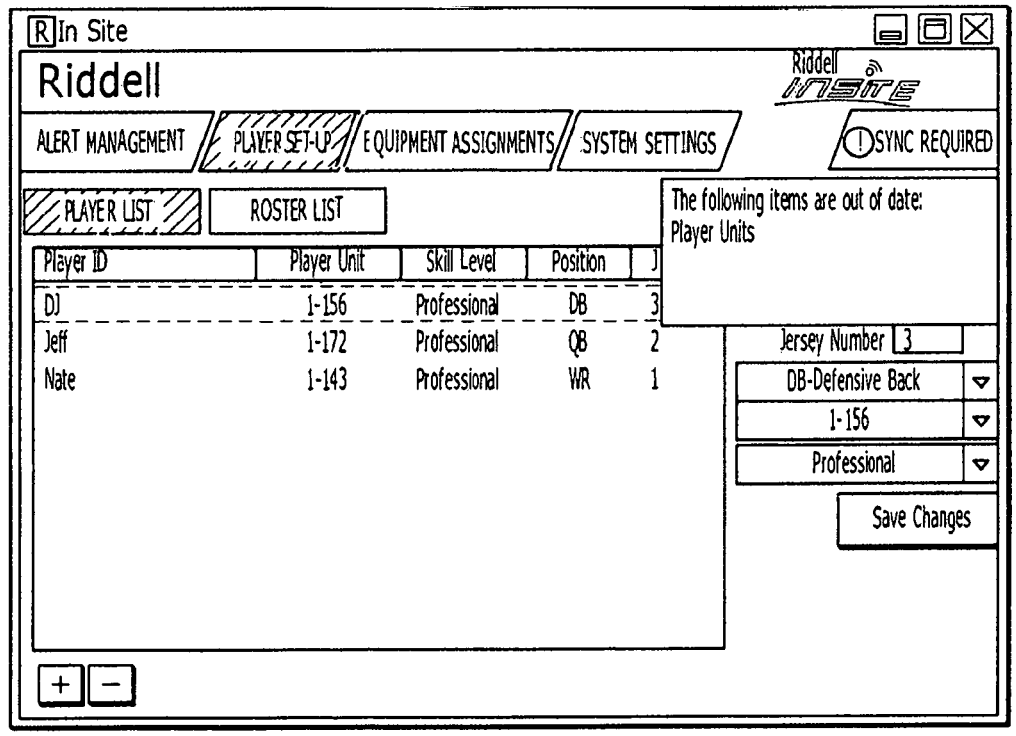

FIG. 8H illustrates an exemplary UI 2000H allowing the user to identify the in-helmet unit(s) 1200 that require a sync and the process for syncing same. To learn which in-helmet unit 1200 among the many configured units 1200 require a sync, the user can hover cursor over the "SYNC REQUIRED" tab on the UI 2000H. If one or more in-helmet units 1200 require a sync, these in-helmet units 1200 will appear in the drop down list. The user can then select the necessary in-helmet units 1200 in the list to start the synchronization wizard. The UI 2000H may alert the user to ensure that there is an alert unit 1120 connected to the PC terminal 1130 before selecting a sync for the identified in-helmet unit 1200. Next, the user is instructed to hold the round sync button for the selected player helmet 1110 for prolonged period of time (e.g., 5 seconds). Once the orange light starts to blink, the selected player helmet 1110 is synced with the in-helmet unit 1200. The user can then continue with the wizard instructions noted above until all of the identified in-helmet units 1200 are synced.

Figure 8I:
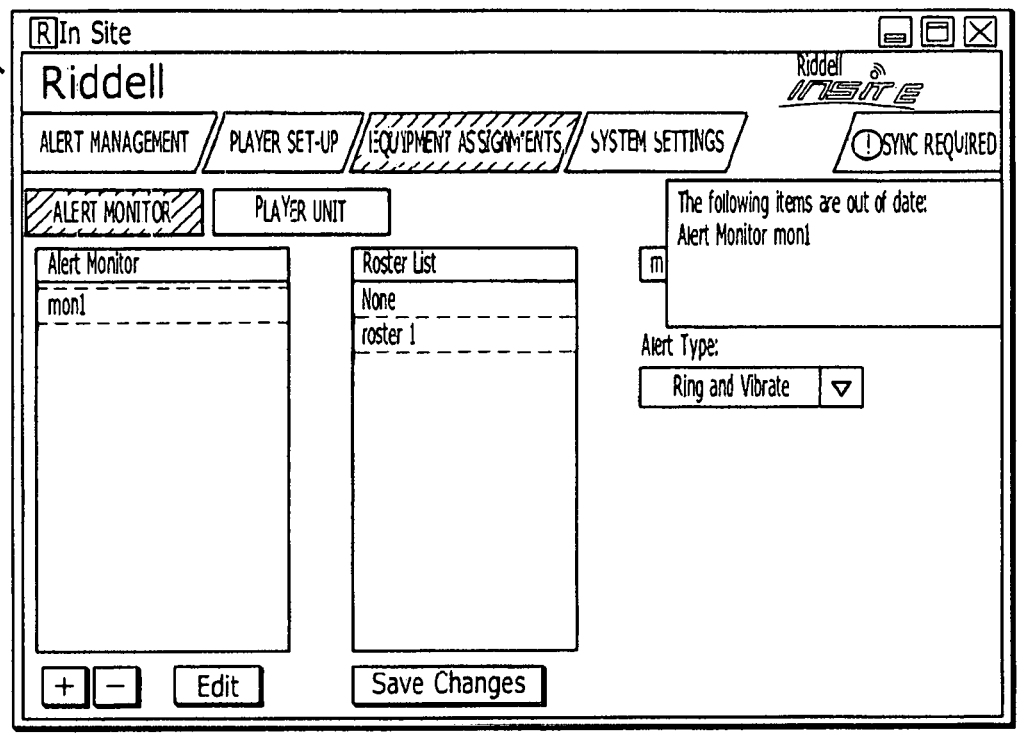

FIG. 8I illustrates an exemplary UI 2000I allowing the user to identify the alert units 1120 that require a sync and to sync the identified alert units 1120. To complete the sync required for alert units 1120, the user can hover cursor over the "SYNC REQUIRED" tab on the UI 2000I. If one or more alert units 1120 require a sync, alert units 1120 will appear in the drop down menu. The user can then select one of the identified alert units 1120 while the alert unit 1120 is connected to the user terminal 1130 to sync the alert unit 1120. Once the "SYNC REQUIRED" image is grayed out, the sync is completed and the user is ready to use the system 1100.

Figure 9:
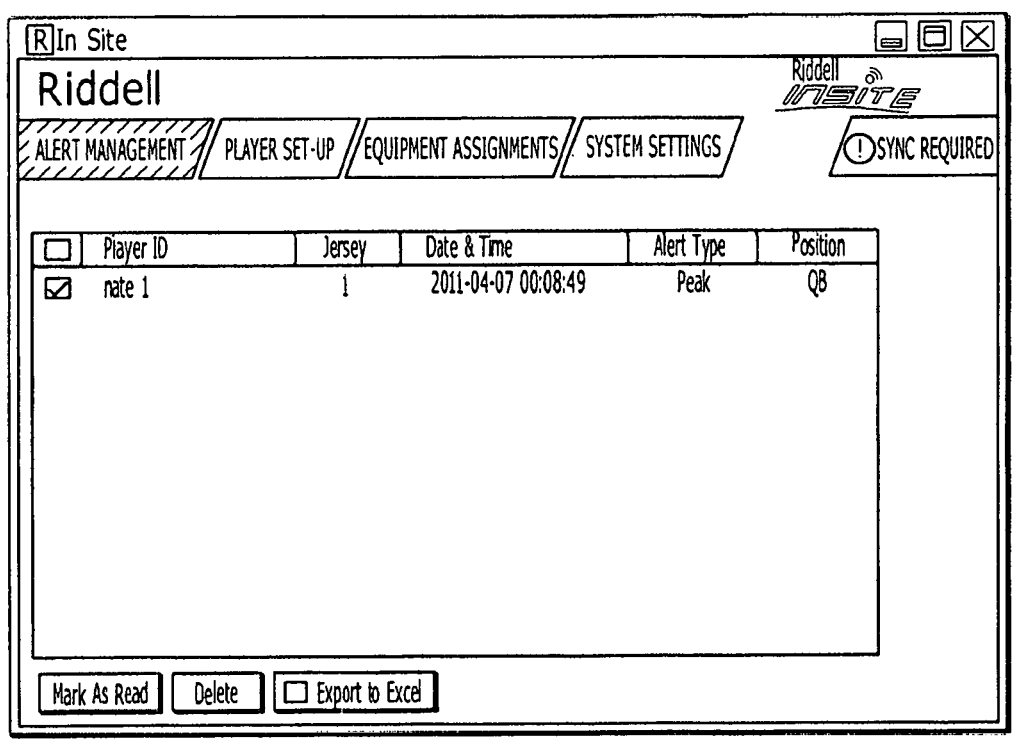
FIG. 9 illustrates an exemplary UI allowing the user to download alerts.

FIG. 9 illustrates an exemplary UI 2100 allowing the user to download alerts. To download alerts, the user opens PMS application and connects the alert unit 1120 to the computer. The PMS application will then automatically check the alert unit 1120 for new alerts and downloads and displays them to the "ALERT MANAGEMENT" tab. New alerts may be shown as bold and checked. Bolded alerts are considered "Unread" alerts. Selecting them will un-bold the text. Also, selecting "Mark As Read" button will un-bold all check alerts. Selecting the "Delete" button will remove all checked alerts from the list. To save alerts, user can export the data to the excel by selecting "Export to Excel" button on UI 2100. Selecting "Export to Excel" creates a comma delimited file of all checked alerts. The columns in the file correspond with the columns in the software.

Figure 10:
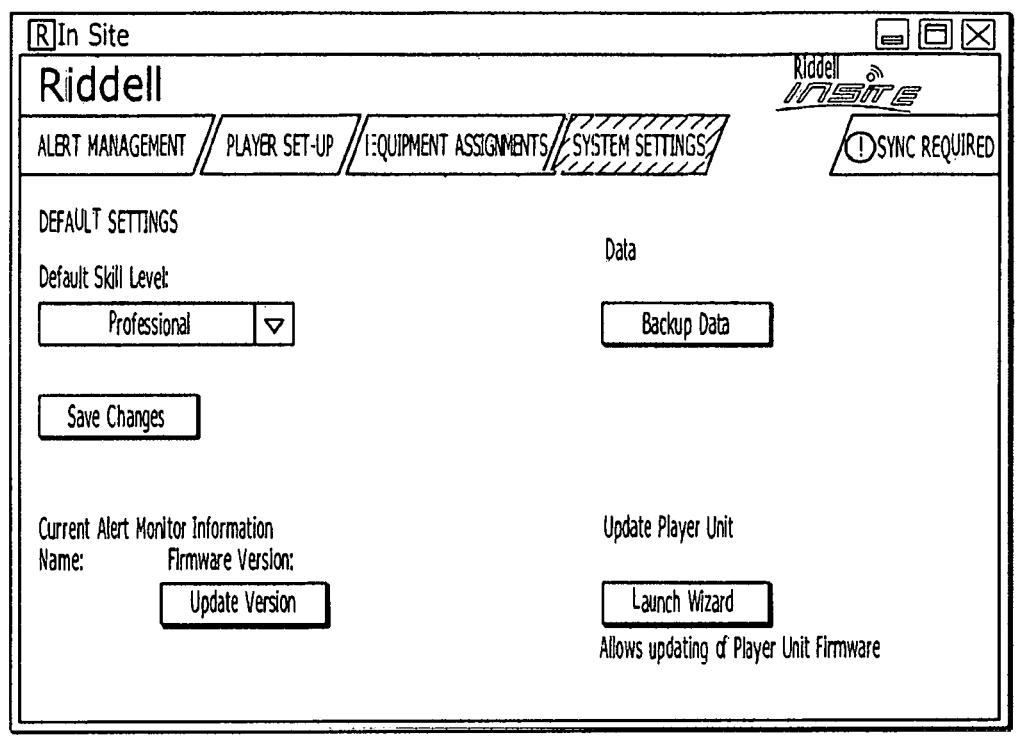
FIG. 10 illustrates an exemplary UI allowing the user to modify system settings.

FIG. 10 illustrates an exemplary UI 2200 allowing the user to modify system settings. To do so, the user selects "SYSTEM SETTINGS" on the UI 2200, which results in display of "default settings" icon and "data" icon. The "default settings" icon allows the user to set the default skill level for newly created player. The "data" icon allows the user for backing up of the database. This can be used for general disaster recovery or to switch computers and keep the data. The bottom section of UI 2200 allows for updating of firmware for both in-helmet units 1200 and alert units 1120.

Figure 11:
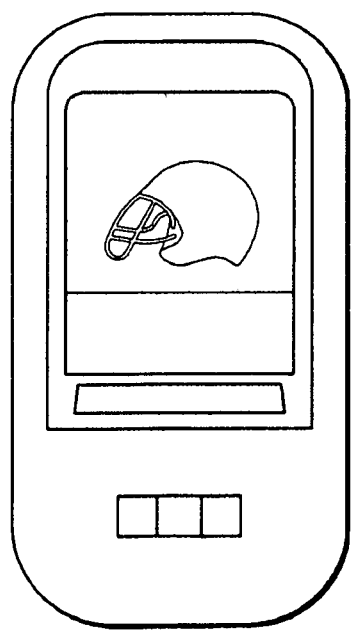
FIG. 11 illustrates an exemplary alert unit.

FIG. 11 illustrates an exemplary alert unit 1120. The alert unit 1120 is configured to display three types of alert signals: sound, visual (e.g., blinking light on alert unit), and vibration. The alert signal is received when the alert unit 1120 is within 50 yards of the in-helmet unit 1200. The alert signal is stored within the control module 1230 of the in-helmet unit 1200 until the alert unit 1120 is within range. Once the alert unit 1120 is turned ON, it will display a standard menu. The menu includes "Alerts," "Check-ins," and "Settings" options. The selection of the "Alerts" option allows the user to view the existing alerts for various players. The alerts may identify the name of the player and the date the alert was generated. The user can select an alert specific to a player by clicking on the name of the specific player. The user can then see the type of alert (e.g., single impact or cumulative impact) for the specific player. The selection of "Check-in" options allows the user to check-in players that are present today among the players in the roster. Selecting this option allows the user to also view players who are absent today among the players in the roster. The selection of "settings" allows the user to set the date and time in the alert unit 1120.

This disclosure may also include a method of evaluating and treating players that experience an Alert Event. A signaling device may be programmed with interactive software (e.g., interactive software programs, signaling device software, interactive wizards, interactive wizard programs, wizard software, wizard programs, wizard software programs, wizard software package) that assures best practices are followed in the treatment and documentation of injuries, such as mild traumatic brain injuries (MTBI). The interactive software may include a bundle of team management programs which enables the signaling device to store all team data, including medical histories and testing baselines. The interactive software also provides the signaling device with an active response protocol for guiding sideline personnel through appropriate examination procedures and recording the results. For example, when an Alert Event occurs and the relevant player is brought to the sideline for evaluation, the signaling device can display the individual's head-injury history, the results of previous evaluations and other pertinent medical data. With the assistance of the interactive software, the signaling device prompts the medical staff member to conduct the appropriate sideline examination, records the responses, compares the results to established baselines and prompts either further testing or a play/no-play decision. The interactive software further includes a bundle of team management tools that includes a roster program which contains all the basic information about each individual player: e.g., contact information, which sports they play (including position and jersey number), emergency information, relevant sizes, equipment issues and availability to play. Information can be stored and sorted in a variety of ways, such as by team, person item and size. The interactive software may also include a session manager program that allows the coaching staff to document incidents as they occur during a practice or a game. The appropriate information about the team, players and conditions is entered at the beginning of each session. Then, as injuries occur, the interactive software provides a template for recording injury data on a per player basis. The data and results stored on the device can be uploaded to the database wherein authorized users can access same for team management and player evaluation functions.

The database 1150 may be configured to store and provide access to parameter data measured by the in-helmet unit (or monitoring unit) 1200 and calculated data from any of the control module 1230, the alert unit 1120, and the user terminal 1130. For example, the database 1150 serves as a team administrator database for the athletic department of a college or university, wherein the database 1150 functions as an interactive clearinghouse or warehouse for all athlete information shared among various departments or sports. The database 1150 allows the user to create players and assign player units to players, to review historical alerts and to update new firmware on both alert monitors and player units. No internet connection is required except to download new firmware and/or software. The database 1150 may be internet enabled to provide remote access to authorized users, including coaches, trainers, equipment managers and administrators, which allows the users to keep abreast of changes in players' status. The database 1150 also provides a host of administrative and management tools for the team and administrative staff. The database 1150 can be a component of the college's broader computer network system and interact with other databases associated with the system 1100. On a smaller level, such as that found in high schools, the database 1150 can be located on the user terminal 1130, wherein personnel associated with the high school have access, either direct or remote.

As known in the data processing and communications arts, a general-purpose computer typically comprises a central processor or other processing device, an internal communication bus, various types of memory or storage media (RAM, ROM, EEPROM, cache memory, disk drives etc.) for code and data storage, and one or more network interface cards or ports for communication purposes. The software functionalities involve programming, including executable code as well as associated stored data. The software code is executable by the general-purpose computer that functions as the user terminal 1130. In operation, the code is stored within the general-purpose computer platform. At other times, however, the software may be stored at other locations and/or transported for loading into the appropriate general-purpose computer system.

Figure 12:
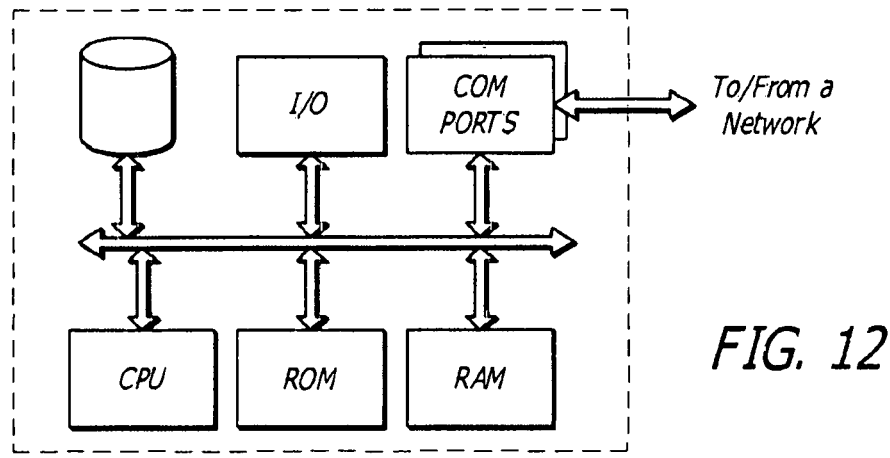
FIG. 12 illustrates a network or host computer platform, as may typically be used to implement a server.
Figure 13:
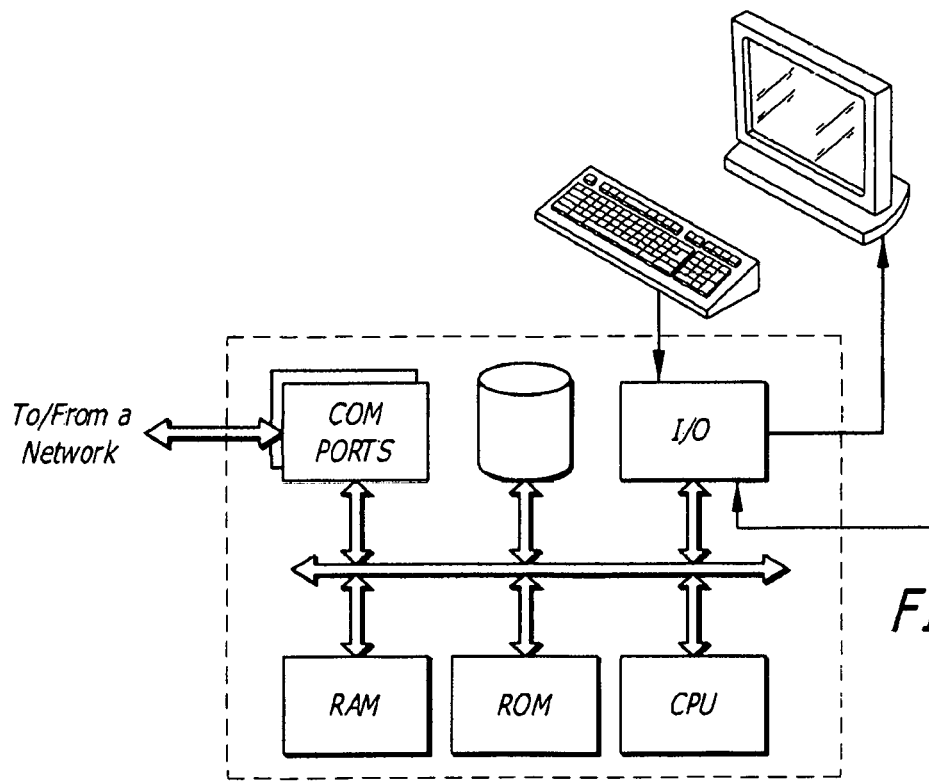
FIG. 13 illustrates a computer with user interface elements, as may be used to implement a personal computer.

FIGS. 12 and 13 provide functional block diagram illustrations of general purpose computer hardware platforms. FIG. 12 illustrates a network or host computer platform, as may typically be used to implement a server. FIG. 13 depicts a computer with user interface elements, as may be used to implement a personal computer or other type of work station or terminal device, although the computer of FIG. 13 may also act as a server if appropriately programmed. It is believed that those skilled in the art are familiar with the structure, programming and general operation of such computer equipment and as a result the drawings should be self-explanatory.

A server, for example, includes a data communication interface for packet data communication. The server also includes a central processing unit (CPU), in the form of one or more processors, for executing program instructions. The server platform typically includes an internal communication bus, program storage and data storage for various data files to be processed and/or communicated by the server, although the server often receives programming and data via network communications. The hardware elements, operating systems and programming languages of such servers are conventional in nature, and it is presumed that those skilled in the art are adequately familiar therewith. The server functions may be implemented in a distributed fashion on a number of similar platforms, to distribute the processing load.

Hence, aspects of the methods for operating the system 1100 outlined above may be embodied in programming. Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the methods for enabling operation of system 1100. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

For example, the system 1100 may be equipped with an automatic on/off system that detects the system is in use. This feature prevents the potential of false alarms due to handling helmet outside the field use and provides extended battery life (1+ season of use without a battery change). The system 1100 is an Omni-Directional device. To this end, the system 1100 has five distinct channels. The distinction of channels enables the calculation of not only the severity of the impact, but also the location of impact. This location estimate is an important component of the HITsp calculation. The impact location factor increases the sensitivity of the over-exposure threshold to providing direction on the possibility of concussion.

In another implementation, the shake sensor is used for pairing, power up, power down. The shake sensor is a motion sensor. The system will go to sleep if there is no motion.

In another implementation, as noted above, when a single or multiple impact exceeds the threshold (either a single threshold or cumulative threshold), an alert is wirelessly transmitted from the in-helmet units 1200 to the alert unit 1120. The transmission from the in-helmet units 1200 to the alert unit 1120 may be encoded with the player's unique identifier.

In one implementation, the alert unit provides acknowledgment of the alert unit to the player helmet. The player helmet may not check-in with alert unit during the course of play, and the alert unit does not query the player helmet during the course of play. However, the player helmet may check with the alert unit once every day independent of alert. This allows the player helmet to update time and provides a basic check of system function by the user with the alert unit. Update time is to sync times between player helmet and alert unit. Alert times are therefore relative to alert unit times, which is realistically actual time. The alert unit gets updated from the computer every time it is connected, which keeps time drift very low. Also, time accuracy is maintained on the alert unit when not connected to a PC by using an onboard real-time clock.

In another implementation, the system can identify and report improper tackling technique, i.e., spearing (head first) tackling. To this end, the system may record impact frequency by magnitude and location and report that information back to the user.

Other implementations are contemplated.

The invention claimed is:

1. A system for transmitting impact alerts to a portable alert unit based upon impacts received by a specific player in a subset of multiple players that are engaged in play of a contact sport, the system comprising:
   a plurality of monitoring units, each individual monitoring unit configured to be worn by one of the specific players in the subset of multiple players, said monitoring unit is configured to: (i) transmit a first alert that is based upon a single impact value and (ii) transmit a second alert that is based upon a cumulative impact value, wherein the monitoring unit is configured to generate the single impact value when the monitoring unit measures a value that exceeds a first predetermined threshold, wherein the monitoring unit is configured to generate the cumulative impact value from an accumulation of single impact values that exceed a second predetermined threshold while the player is engaged in playing the contact sport over an extended period of time, wherein the monitoring unit is configured to transmit the first alert to a portable alert unit when the single impact value exceeds a third predetermined threshold, and wherein the monitoring unit is configured to transmit the second alert when the cumulative impact value exceeds a fourth predetermined threshold.

2. The monitoring system of claim 1, wherein the monitoring unit is comprised of a sensor assembly and a control module, said control module includes a telemetry unit that is configured to wirelessly transmit either the first alert or the second alert to the portable alert unit.

3. The monitoring system of claim 2 further comprising:
a protective sports helmet configured to be worn by the specific player, wherein the sports helmet includes: (i) an internal padding assembly and (ii) overliner that is configured to be positioned between the specific player's head and the internal padding assembly when the sports helmet is worn by the specific player; and
wherein the sensor assembly is configured to be positioned within the overliner.

4. The monitoring system of claim 3, wherein the sensor assembly further comprises a front sensor positioned adjacent a front region of the sports helmet, a rear sensor positioned adjacent a rear region of the sports helmet, a left sensor positioned adjacent a left region of the sports helmet, a right sensor positioned adjacent a right region of the sports helmet and a top sensor positioned adjacent a top region of the sports helmet.

5. The monitoring system of claim 1, wherein the value measured by the monitoring unit is a pressure measurement resulting from an impact that the specific player received during the play of the contact sport.

6. The monitoring system of claim 1, wherein the single impact value is a variable that is calculated by weighting impact measurements that were recorded by the monitoring unit during an impact that the specific player received during the play of the contact sport.

7. The monitoring system of claim 6, wherein the impact measurements include at least three of the following: (i) linear acceleration, (ii) rotational acceleration, (iii) impact direction, (iv) impact location, (v) Head Injury Criterion, (vi) Gadd Severity Index.

8. The monitoring system of claim 1, wherein the monitoring unit is configured to decrease the cumulative impact value based on an exponential decay function.

9. The monitoring system of claim 1, wherein both the second predetermined threshold and the third predetermined threshold are weighted to account for the player's skill level and the player's position.

10. The monitoring system of claim 1, wherein the transmission of the first and second alerts to the portable alert unit includes the transmission of alert information, said alert information includes: (i) the specific player's identification, (ii) whether the alert was a first alert or a second alert, and (iii) a time either the first alert or the second alert occurred.

11. The monitoring system of claim 1, further comprising a database that is configured to store the alert information that was received by the portable alert unit.

12. The monitoring system of claim 11, wherein a remote terminal is configured to identify improper tackling techniques based in part upon the alert information that is stored in the database.

13. A system for monitoring impacts received by a player engaged in play of a contact sport, the system comprising:
a protective sports equipment configured to be worn adjacent to the player's body part while the player is engaged in playing the contact sport;
a monitoring unit positioned within the sports equipment and associated with the player, the monitoring unit having both a sensor assembly and a control module,
wherein the monitoring unit is configured to generate a single impact value when the monitoring unit determines a pressure measurement that exceeds a first predetermined threshold,
wherein the monitoring unit is configured to generate a cumulative impact value from an accumulation of single impact values that exceed a second predetermined threshold while the player is engaged in playing the contact sport over an extended period of time, and
wherein the monitoring unit is configured to transmit a first alert to a portable alert unit when the single impact value exceeds a third predetermined threshold and is configured to transmit a second alert when the cumulative impact value exceeds a fourth predetermined threshold;
the portable alert unit configured to receive any of the first alert and second alert transmitted from the monitoring unit and being further configured to display information relating to both the received first alert or second alert and the identification of the player associated with the received first alert or second alert; and
a remote terminal configured to receive any of the first alert and second alert from the portable alert unit and being further configured to display information relating to both the received first alert or second alert and an identification of the player associated with the received first alert or second alert.

14. The system of claim 13, wherein the protective sports equipment is a helmet that is configured to be worn by the player, wherein the sports helmet includes: (i) an internal padding assembly and (ii) overliner that is configured to be positioned between the player's head and the internal padding assembly when the sports helmet is worn by the player; and
wherein the sensor assembly is configured to be positioned within the overliner.

15. The system of claim 14, wherein the sensor assembly further comprises a front sensor positioned adjacent a front region of the sports helmet, a rear sensor positioned adjacent a rear region of the sports helmet, a left sensor positioned adjacent a left region of the sports helmet, a right sensor positioned adjacent a right region of the sports helmet and a top sensor positioned adjacent a top region of the sports helmet.

16. The system of claim 13, wherein the single impact value is a variable that is calculated by weighting impact measurements that were recorded by the monitoring unit during an impact that the specific player received during the play of the contact sport.

17. The system of claim 16, wherein the impact measurements include at least two of the following: (i) linear acceleration, (ii) rotational acceleration, (iii) impact direction, (iv) impact location, (v) Head Injury Criterion, (vi) Gadd Severity Index.

18. The system of claim 13, wherein the monitoring unit is configured to decrease the cumulative impact value based on an exponential decay function.

19. The system of claim 13, wherein both the second predetermined threshold and the third predetermined threshold are weighted to account for the player's skill level and the player's position.

20. The system of claim 13, the remote terminal configured to identify improper tackling techniques based in part upon information relating to both the received first alert or second alert and the identification of the player associated with the received first alert or second alert.

21. The system of claim 13, wherein the remote terminal is further configured to report identified improper tackling techniques to authorized users.

22. The system of claim 13, wherein the remote terminal is an internet enabled device that allows authorized users to remotely access information relating to both the received first alert or second alert and the identification of the player associated with the received first alert or second alert.

23. The system of claim 13, wherein the remote terminal is an internet enabled device that allows authorized users to remotely review historical information relating to both the received first alert or second alert and the identification of the player associated with the received first alert or second alert.

24. A system for monitoring impacts received by a player engaged in play of a contact sport, the system comprising:
a monitoring unit positioned within a piece of protective sports equipment worn by the player, the monitoring unit including a sensor assembly and a control module, the monitoring unit being configured to:
(i) generate a single impact value when the monitoring unit measures a value that exceeds a first predetermined threshold,
(ii) generate a cumulative impact value from an accumulation of single impact values that exceed a second predetermined threshold while the player is engaged in playing the contact sport over an extended period of time, and
(iii) transmit a cumulative impact alert when the cumulative impact value exceeds a predetermined cumulative impact threshold.

25. The monitoring system of claim 24, wherein the control module includes a telemetry unit that is configured to wirelesly transmit the cumulative impact alert to the portable alert unit.

26. The monitoring system of claim 24, further comprising:
a protective sports helmet configured to be worn by the specific player, wherein the sports helmet includes: (i) an internal padding assembly and (ii) overliner that is configured to be positioned between the specific player's head and the internal padding assembly when the sports helmet is worn by the specific player; and
wherein the sensor assembly is configured to be positioned within the overliner.

27. The monitoring system of claim 26, wherein the sensor assembly further comprises a front sensor positioned adjacent a front region of the sports helmet, a rear sensor positioned adjacent a rear region of the sports helmet, a left sensor positioned adjacent a left region of the sports helmet, a right sensor positioned adjacent a right region of the sports helmet and a top sensor positioned adjacent a top region of the sports helmet.

28. The monitoring system of claim 24, wherein the value measured by the monitoring unit is a pressure measurement resulting from an impact that the player received during the play of the contact sport.

29. The monitoring system of claim 24, wherein the single impact value is a variable that is calculated by weighting impact measurements that were determined by the monitoring unit during an impact that the player received during the play of the contact sport.

30. The monitoring system of claim 24, wherein the monitoring unit is configured to decrease the cumulative impact value based on an exponential decay function.

31. The monitoring system of claim 25, further comprising a database that is configured to store alert information regarding the cumulative impact alert that was received by the portable alert unit.

32. The monitoring system of claim 31, further comprising a remote terminal that is configured to identify improper tackling techniques based in part upon the alert information that is stored in the database.

* * * * *